United States Patent
Shih et al.

[11] Patent Number: 5,945,428
[45] Date of Patent: Aug. 31, 1999

[54] SUBSTITUTED OXIMES, HYDRAZONES AND OLEFINS AS NEUROKININ ANTAGONISTS

[75] Inventors: Neng-Yang Shih, North Caldwell; Gregory A. Reichard, Morris Plains; Robert G. Aslanian, Rockaway, all of N.J.

[73] Assignee: Schering Corporation, Kenilworth, N.J.

[21] Appl. No.: 08/960,724

[22] Filed: Oct. 30, 1997

Related U.S. Application Data

[60] Provisional application No. 60/029,966, Nov. 1, 1996.

[51] Int. Cl.$^6$ .................. A61K 31/44; C07D 221/00
[52] U.S. Cl. .................. 514/278; 546/16; 546/17
[58] Field of Search .................. 514/278; 546/16, 546/17

[56] References Cited

U.S. PATENT DOCUMENTS

| | | | |
|---|---|---|---|
| 5,350,852 | 9/1994 | Emonds-Alt et al. | 544/336 |
| 5,434,158 | 7/1995 | Shah | 514/278 |
| 5,654,316 | 8/1997 | Carruthers et al. | 514/307 |
| 5,688,960 | 11/1997 | Shankar | 546/202 |
| 5,691,362 | 11/1997 | McCormick et al. | 514/339 |
| 5,696,267 | 12/1997 | Reichard et al. | 546/217 |

FOREIGN PATENT DOCUMENTS

| | | |
|---|---|---|
| 630887 | 12/1994 | European Pat. Off. |
| 0 699 674 | 3/1996 | European Pat. Off. |
| WO 94/17045 | 8/1994 | WIPO |
| WO94/20500 | 9/1994 | WIPO |
| WO 94/29309 | 12/1994 | WIPO |
| WO 96/10568 | 4/1996 | WIPO |
| WO 96/34857 | 11/1996 | WIPO |

OTHER PUBLICATIONS

Maggi et al, *Eur. J. Pharmacol.*, 166, (1989), pp. 435–440.
Ellis et al, *J. Pharmacol. Exp. Ther.*, 267, 1 (1993), pp. 95–101.
Furchgott, *Pharm. Rev.*, 7 (1955), pp. 183–265.
Arunlakshana et al, *Brit. J. Pharmacol.*, 14, 48 (1959), pp. 48–58.
Danko et al, *Pharmacol. Comm.*, 1, 3 (1992), pp. 203–209.
Chung et al, *Molecular Pharmacol.*, 48 (1995), pp. 711–716.
Ong, et al, *J. Med. Chem.*, 26 (1983), pp. 981–986.

*Primary Examiner*—Richard L. Raymond
*Assistant Examiner*—Pavanaram K Sripada
*Attorney, Agent, or Firm*—Anita W. Magatti

[57] ABSTRACT

Compound represented by the structural formula

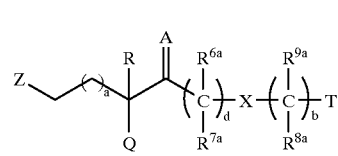

I or a pharmaceutically acceptable salt thereof, wherein:
  a is 0, 1, 2 or 3;
  b, d and e are independently 0, 1 or 2;
  R is H, $C_{1-6}$ alkyl, —OH or $C_2$–$C_6$ hydroxyalkyl;
  A is an optionally substituted oxime, hydrazone or olefin;
  X is a bond, —C(O)—, —O—, —$NR^6$—, —$S(O)_e$—, —$N(R^6)C(O)$—, —$C(O)N(R^6)$— —$OC(O)NR^6$—, —$OC(=S)NR^6$—, —$N(R^6)C(=S)O$—, —C(=$NOR^1$)—, —$S(O)_2N(R^6)$—, —$N(R^6)S(O)_2$—, —$N(R^6)C(O)O$— or —OC(O)—;
  T is H, phthalimidyl, aryl, heterocycloalkyl, heteroaryl, cycloalkyl or bridged cycloalkyl;
  Q is —$SR^6$, —$N(R^6)(R^7)$, —$OR^6$, phenyl, naphthyl or heteroaryl;
  $R^{6a}$, $R^{7a}$, $R^{8a}$, $R^{9a}$, $R^6$ and $R^7$ are H, $C_{1-6}$ alkyl, $C_2$–$C_6$ hydroxyalkyl, $C_1$–$C_6$ alkoxy-$C_1$–$C_6$ alkyl, phenyl or benzyl; or $R^6$ and $R^7$, together with the nitrogen to which they are attached, form a ring;
  $R^{9a}$ is $R^6$ or —$OR^6$; and
  Z is spiro-substituted piperidinyl or substituted piperazinyl wherein aryl, heterocycloalkyl, heteroaryl, cycloalkyl and bridged cycloalkyl groups are optionally substituted; methods of treating asthma, cough, bronchospasm, imflammatory diseases, and gastrointestinal disorders with said compounds, and pharmaceutical compositions comprising said compounds are disclosed.

12 Claims, No Drawings

SUBSTITUTED OXIMES, HYDRAZONES AND OLEFINS AS NEUROKININ ANTAGONISTS

CROSS REFERENCE TO RELATED APPLICATIONS

This application claims the benefit of U.S. Provisional Application No. 60/029,966, filed Nov. 1, 1996.

BACKGROUND OF THE INVENTION

The present invention relates to a genus of substituted oximes, hydrazones and olefins useful as antagonists of tachykinin receptors, in particular as antagonists of the neuropeptides neurokinin-1 receptor ($NK_1$) and/or neurokinin-2 receptor ($NK_2$) and/or neurokinin-3 receptor (NK3).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, spiro-substituted azacycles were disclosed in WO 94/29309, published Dec. 22, 1994, and in WO 94/17045, published Aug. 4, 1994; substituted aryl piperazines were disclosed in WO 96/10568, published Apr. 11, 1996.

SUMMARY OF THE INVENTION

Compounds of the present invention are represented by the formula I

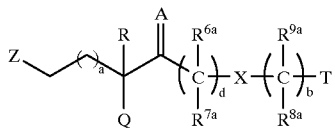

I or a pharmaceutically acceptable salt thereof, wherein:

a is 0, 1, 2 or 3;

b and d are independently 0, 1 or 2;

R is H, $C_{1-6}$ alkyl, $-OR^6$ or $C_2-C_6$ hydroxyalkyl;

A is $=N-OR^1$, $=N-N(R^2)(R^3)$, $=C(R^{11})(R^{12})$ or $=NR^{25}$;

X is a bond, $-C(O)-$, $-O-$, $-NR^6-$, $-S(O)_e-$, $-N(R^6)C(O)-$, $-C(O)N(R^6)-$, $-OC(O)NR^6-$, $-OC(=S)NR^6-$, $-N(R^6)C(=S)O-$, $-C(=NOR^1)-$, $-S(O)_2N(R^6)-$, $-N(R^6)S(O)_2-$, $-N(R^6)C(O)O-$ or $-OC(O)-$, provided that when d is 0, X is a bond, $-C(O)-$, $-NR^6-$, $-C(O)N(R^6)-$, $-N(R^6)C(O)-$, $-OC(O)NR^6-$, $-C(=NOR^1)-$, $-N(R^6)C(=S)O-$, $-OC(=S)NR^6-$, $-N(R^6)S(O)_2-$ or $-N(R^6)C(O)O-$; provided that when A is $=C(R^{11})(R^{12})$ and d is 0, X is not $-NR^6-$ or $-N(R^6)C(O)-$; and provided that when A is $=NR^{25}$, d is 0 and X is $-NR^6-$ or $-N(R^6)C(O)-$;

T is H, $R^4$-aryl, $R^4$-heterocycloalkyl, $R^4$-heteroaryl, phthalimidyl, $R^4$-cycloalkyl or $R^{10}$-bridged cycloalkyl;

Q is $R^5$-phenyl, $R^5$-naphthyl, $-SR^6$, $-N(R^6)(R^7)$, $-OR^6$ or $R^5$-heteroaryl, provided that when Q is $-SR^6$, $-N(R^6)(R^7)$ or $-OR^6$, R is not $-OR^6$;

$R^1$ is H, $C_{1-6}$ alkyl, $-(C(R^6)(R^7))_n-G$, $-G^2$, $-(C(R^6)(R^7))_p-M-(C(R^{13})(R^{14}))_n-(C(R^8)(R^9))_u-G$, $-C(O)N(R^6)-(C(R^{13})(R^{14}))_n-(C(R^8)(R^9))_u-G$ or $-(C(R^6)(R^7))_p-M-(R^4$-heteroaryl);

$R^2$ and $R^3$ are independently selected from the group consisting of H, $C_{1-6}$ alkyl, $-CN$, $-(C(R^6)(R^7))_n-G$, $-G^2$, $-C(O)-(C(R^8)(R^9))_n-G$ and $-S(O)_eR^{13}$; or $R^2$ and $R^3$, together with the nitrogen to which they are attached, form a ring of 5 to 6 members, wherein 0, 1 or 2 ring members are selected from the group consisting of $-O-$, $-S-$ and $-N(R^{19})-$;

$R^4$ and $R^5$ are independently 1–3 substituents independently selected from the group consisting of H, halogeno, $-OR^6$, $-OC(O)R^6$, $-OC(O)N(R^6)(R^7)$, $-N(R^6)(R^7)$, $C_{1-6}$ alkyl, $-CF_3$, $-C_2F_5$, $-COR^6$, $-CO_2R^6$, $-CON(R^6)(R^7)$, $-S(O)_eR^{13}$, $-CN$, $-OCF_3$, $-NR^6CO_2R^{16}$, $-NR^6COR^7$, $-NR^8CON(R^6)(R^7)$, $R^{15}$-phenyl, $R^{15}$-benzyl, $NO_2$, $-N(R^6)S(O)_2R^{13}$ or $-S(O)_2N(R^6)(R^7)$; or adjacent $R^4$ substituents or adjacent $R^5$ substituents can form a $-O-CH_2-O-$ group; and $R^4$ can also be $R^{15}$-heteroaryl;

$R^6$, $R^7$, $R^8$, $R^{6a}$, $R^{7a}$, $R^{8a}$, $R^{13}$ and $R^{14}$ are independently selected from the group consisting of H, $C_{1-6}$ alkyl, $C_2-C_6$ hydroxyalkyl, $C_1-C_6$ alkoxy-$C_1-C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of $-O-$, $-S-$ and $-N(R^{19})-$;

$R^9$ and $R^{9a}$ are independently selected from the group consisting of $R^6$ and $-OR^6$ $R^{10}$ and $R^{10a}$ are independently selected from the group consisting of H and $C_{1-6}$ alkyl;

$R^{11}$ and $R^{12}$ are independently selected from the group consisting of H, $C_1-C_6$ alkyl, $-CO_2R^6$, $-OR^6$, $-C(O)N(R^6)(R^7)$, $C_1-C_6$ hydroxyalkyl, $-(CH_2)_r-OC(O)R^6$, $-(CH_2)_r-OC(O)CH=CH_2$, $-(CH_2)_r-O(CH_2)_s-CO_2R^6$, $-(CH_2)_r-O-(CH_2)_s-C(O)N(R^6)(R^7)$ and $-(CH_2)_r-N(R^6)(R^7)$;

$R^{15}$ is 1 to 3 substituents independently selected from the group consisting of H, $C_1-C_6$ alkyl, $C_1-C_6$ alkoxy, $C_1-C_6$ alkylthio, halogeno, $-CF_3$, $-C_2F_5$, $-COR^{10}$, $-CO_2R^{10}$, $-C(O)N(R^{10})_2$, $-S(O)_eR^{10a}$, $-CN$, $-N(R^{10})COR^{10}$, $-N(R^{10})CON(R^{10})_2$ and $-NO_2$;

$R^{16}$ is $C_{1-6}$ alkyl, $R^{15}$-phenyl or $R^{15}$-benzyl;

$R^{19}$ is H, $C_1-C_6$ alkyl, $-C(O)N(R^{10})_2$, $-CO_2R^{10}$, $-(C(R^8)(R^9))_f-CO_2R^{10}$ or $-(C(R^8)(R^9))_u-C(O)N(R^{10})_2$;

f, n, p, r and s are independently 1–6;

u is 0–6;

G is selected from the group consisting of H, $R^4$-aryl, $R^4$-heterocycloalkyl, $R^4$-heteroaryl, $R^4$-cycloalkyl, $-OR^6$, $-N(R^6)(R^7)$, $-COR^6$, $-CO_2R^6$, $-CON(R^7)(R^9)$, $-S(O)_eR^{13}$, $-NR^6CO_2R^{16}$, $-NR^6COR^7$, $-NR^8CON(R^6)(R^7)$, $-N(R^6)S(O)_2R^{13}$, $-S(O)_2N$ (R⁶)(R⁷), —OC(O)R⁶, —OC(O)N(R⁶)(R⁷), —C(=NOR⁸)N(R⁶)(R⁷), —C(=NR²⁵)N(R⁶)(R⁷), —N(R⁸)C(=NR²⁵)N(R⁶)(R⁷), —CN, —C(O)N(R⁶)OR⁷, and —C(O)N(R⁹)—(R⁴-heteroaryl), provided that when n is 1 and u is 0, or when R⁹ is —OR⁶, G is not —OH or —N(R⁶)(R⁷);

M is selected from the group consisting of a double bond, —O—, —N(R⁶)—, —C(O)—, —C(R⁶)(OR⁷)—, —C(R⁸)(N(R⁶)(R⁷))—, —C(=NOR⁶)N(R⁷)—, —C(N(R⁶)(R⁷))=NO—, —C(=NR²⁵)N(R⁶)—, —C(O)N(R⁹)—, —N(R⁹)C(O)—, —C(=S)N(R⁹)—, —N(R⁹)C(=S)— and —N(R⁶)C(O)N(R⁷)—, provided that when n is 1, G is not OH or —NH(R⁶); and when p is 2–6, M can also be —N(R⁶)C(=NR²⁵)N(R⁷)— or —OC(O)N(R⁶)—;

G² is R⁴-aryl, R⁴-heterocycloalkyl, R⁴-heteroaryl, R⁴-ccloalkyl, —COR⁶, —CO₂R¹⁶, —S(O)₂N(R⁶)(R⁷) or —CON(R⁶)(R⁷);

e is 0, 1 or 2, provided that when e is 1 or 2, R¹³ and R¹⁰ᵃ are not H;

R²⁵ is H, C₁–C₆ alkyl, —CN, R¹⁵-phenyl or R¹⁵-benzyl;

Z is

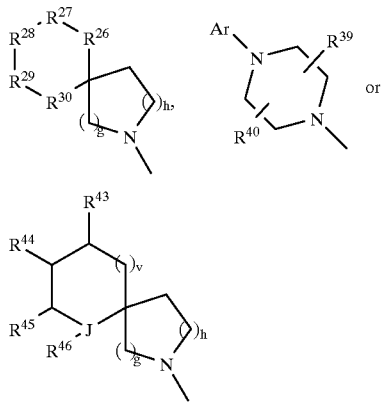

wherein the nitrogen expressly shown above is optionally quaternized with C₁₋₄ alkyl or phenyl-C₁₋₄ alkyl or is optionally present as the N-oxide

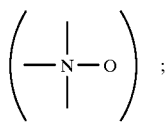

g and h are each independently 0, 1, 2, 3, 4, or 5, with the proviso that g+h is equal to 1, 2, 3, 4, or 5;

R²⁶ is selected from the group consisting of
(1) a covalent bond
(2) C₁₋₃ alkylene, unsubstituted or substituted with a substituent selected from the group consisting of =O, —OH, —OR³⁵, halogeno, —CF₃, phenyl or mono, di or trisubstituted phenyl, wherein the substituents on the phenyl are independently selected from —OH, —CN, halogeno and —CF₃,
(3) S(O)$_k$
(4) (C₁₋₃ alkylene)—S(O)$_k$
(5) S(O)$_k$—(C₁₋₂ alkylene)
(6) S(O)$_k$NH
(7) S(O)$_j$—NR³⁵
(8) S(O)$_j$—NR³⁵—(C₁₋₂ alkylene)
(9) CONH
(10) CONR³⁵—(C₁₋₂ alkylene)
(11) CO₂ and
(12) CO₂—(C₁₋₂ alkylene)
wherein j is 1 or 2 and k is 0, 1 or 2;

R²⁷ is —NR³⁷—, —O—, —S—, —S(O)—, or —SO₂—, with the proviso that when R²⁶ is a covalent bond and R²⁸ is C₁₋₃ alkyl, R²⁷ must be NR³⁷;

R³⁷ is selected from a group consisting of:
(1) H,
(2) C₁₋₈ linear or branched alkyl, unsubstituted, mono-substituted or multiply substituted with —OR³⁵, =O, —NHCOR³⁵, —NR³⁵R³⁶, —CN, —halogeno,—CF₃, —phenyl or substituted phenyl, wherein the substitutents on phenyl are selected from the group consisting of —OH, —CN, halogeno and —CF₃;
(3) S(O)R³⁸, wherein R³⁸ is C₁₋₆ linear or branched alkyl, unsubstituted, mono di or trisubstituted with a substituent selected from the group consisting of =O, —CN, —OR³⁵, —NR³⁵R³⁶, —NR³⁶OR³⁶,—halogeno,—CF₃, —phenyl or mono, di or trisubstituted phenyl, wherein the substituents on the phenyl are independently selected from the group consisting of —OH, =O, —CN, —NR³⁵R³⁶, —NR³⁵COR³⁶, —halogeno, —CF₃ and C₁₋₃ alkyl;
(4) SO₂R³⁸,
(5) COR³⁸,
(6) CO₂R³⁸;
(7) CONR³⁶R³⁸;

R²⁸ is selected from the group consisting of
(1) a covalent bond
(2) C₁₋₃ alkylene, unsubstituted or substituted with a substituent selected from the group consisting of =O, —OR³⁵, halogeno, —CF₃, phenyl or mono, di or trisubstituted phenyl, wherein the substitutents on the phenyl are independently selected from the group consisting of —OR³⁵, halogeno and —CF₃;
(3) S(O)$_k$
(4) (C₁₋₃ alkylene)—S(O)$_k$
(5) S(O)$_k$—(C₁₋₂ alkylene)
(6) NHS(O)$_j$
(7) NH(C₁₋₂ alkylene)—S(O)$_j$
(8) S(O)$_j$NR³⁵
(9) S(O)$_j$—NR³⁵—(C₁₋₂ alkylene)
(10) NHCO—(C₁₋₂ alkylene)
(11) NR³⁵CO
(12) NR³⁵—(C₁₋₂ alkylene)—CO
(13) O(CO) and
(14) (C₁₋₂ alkyl)O(CO);

R²⁹–R³⁰ considered together are 2 adjoining atoms of the ring

said ring being a phenyl, naphthyl or heteroaryl group, and wherein the phenyl, naphthyl or heteroaryl group is unsubstituted, mono, di or tri substituted, wherein heteroaryl is selected from the group consisting of benzimidazolyl, benzofuranyl, benzoxazolyl, furanyl, imidazolyl, indolyl, isoxazolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl and triazolyl; and wherein the substitutents are independently selected from the group consisting of:

(a) $C_{1-6}$ alkyl, branched or unbranched, unsubstituted or mono or disubstituted by hydroxy
(b) =O
(c) $OR^{35}$
(d) halogeno
(e) $CF_3$
(f) $NO_2$
(g) CN
(h) $NR^{35}R^{36}$
(i) $NR^{35}COR^{36}$
(j) $NR^{35}CO_2R^{36}$
(k) $NR^{35}S(O)_jR^{36}$
(l) $CONR^{35}R^{36}$
(m) $COR^{35}$
(n) $CO_2R^{35}$
(o) $S(O)_jR^{35}$
(p) heteroaryl, or mono or di substituted heteroaryl, wherein heteroaryl is as defined above and the substitutents are selected from the group consisting of: $C_{1-6}$ alkyl, branched or unbranched, unsubstituted or mono or disubstituted by OH; =O; $OR^{35}$; $CF_3$; —$NO_2$; CN; $NR^{35}R^{36}$; $NR^{35}COR^{36}$; $NR^{35}CO_2R^{36}$; $NR^{35}S(O)_jR^{36}$; $CONR^{35}R^{36}$; $COR^{35}$; $CO_2R^{35}$; $S(O)_jR^{35}$; and phenyl;

$R^{35}$ and $R^{36}$ are independently selected from:
(a) H,
(b) $C_{1-6}$ alkyl, or mono or disubstituted $C_{1-6}$ alkyl, wherein the substitutents independently selected from the group consisting of phenyl, unsubstituted or substituted with —OH, $C_{1-3}$ alkyl, —CN, halogeno, —$CF_3$ or $C_{1-4}$ alkoxy; —OH; =O; —CN; halogeno; or —$CF_3$;
(c) phenyl, pyridinyl or thiophene, or mono, di or trisubstituted phenyl, pyridinyl or thiophene, wherein the substitutents are independently selected from the group consisting of —OH, $C_{1-4}$ alkyl, —CN, halogeno and —$CF_3$;
(d) $C_{1-3}$ alkyloxy, or
$R^{35}$ and $R^{36}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —$CF_3$;

Ar is selected from the group consisting of phenyl, naphthyl, heteroaryl as defined above, isoquinolyl, benzofuryl, isobenzyofuryl, benzothienyl, isoindolyl, purinyl, triazinyl, benzthiazolyl, imidazopyrazinyl, triazolopyrazinyl, naphthyridinyl, furopyridinyl, thiopyranopyrimidyl and the 5-oxide and 5-dioxide thereof, pyridazinyl, quinazplinyl, pteridinyl, triazolopyrimidyl, triazolopyrazinyl, thiapurinyl, oxapurinyl and deazapurinyl, said groups being optionally mono- or di-substituted by sustituents selected from the group consisting of:
(a) $C_{1-3}$ alkyl or $C_{1-3}$ alkyl substituted by =O, OH, $OR^{41}$, halogen, —$CF_3$, phenyl or mono—, d- or tri-substituted phenyl, wherein the substituents on phenyl are selected from the group consisting of OH, CN, halogen and $CF_3$;
(b) —$(CH_2)_nS(O)_k$—$(C_{1-6}$ alkyl), wherein n is 0, 1 or 2
(c) —$(CH_2)_nS(O)_j$—$NHR^{41}$
(d) —$(CH_2)_nS(O)_j$—$NR^{41}$—$(C_{1-6}$ alkyl)
(e) —$(CH_2)_nCONHR^{41}$
(f) —$(CH_2)_nCONR^{41}$—$(C_{1-6}$ alkyl)
(g) —$(CH_2)_nCO_2H$
(h) —$(CH_2)_nCO_2$—$(C_{1-6}$ alkyl)
(i) —$(CH_2)_nNR^{41}R^{42}$
(j) —$(CH_2)_nNH$—$C(O)$—$(C_{1-6}$ alkyl)
(k) —$(CH_2)_nNH$—$C(O)NH_2$
(l) —$(CH_2)_nNH$—$C(O)NH$—$(C_{1-6}$alkyl)
(m) —$(CH_2)_nNH$—$C(O)N$—(di-$C_{1-6}$ alkyl)
(n) —$(CH_2)_nNH$—$S(O)_k$—$(C_{1-6}$ alkyl)
(o) —$(CH_2)_nN$—$(C_{1-3}$ alkyl)—$C(O)$—$N$—(di-$C_{1-6}$ alkyl)
(p) —$(CH_2)_n$—heteroaryl, —$C(O)$—heteroaryl and —$(CH_2)_n$—O—heteroaryl wherein heteroaryl is as defined above and wherein heteroaryl can be optionally substituted by 1 to 3 substituents selected from the group consisting of: $C_{1-6}$ alkyl, branched or unbranched, unsubstituted or mono or disubstituted by hydroxy; =O; $OR^{35}$; halogeno; $CF_3$; $NO_2$; CN; $NR^{35}R^{36}$; $NR^{35}COR^{36}$; $NR^{35}CO_2R^{36}$; $NR^{35}S(O)_jR^{36}$; $CONR^{35}R^{36}$; $COR^{35}$; $CO_2R^{35}$; and $S(O)_jR^{35}$;

$R^{39}$ and $R^{40}$ are independently selected from the group consisting of H, OH, CN, halogen, $CF_3$ and $C_{1-3}$ alkoxy;

$R^{41}$ is
(a) H,
(b) $C_{1-6}$ alkyl, or mono or disubstituted $C_{1-6}$ alkyl, wherein the substitutents independently selected from the group consisting of phenyl; —OH; =O; —CN; halogeno; and —$CF_3$;
(c) phenyl, mono, di or trisubstituted phenyl, wherein the substitutents are independently selected from the group consisting of —OH, $C_{1-3}$ alkyl, —CN, halogeno and —$CF_3$;

$R^{42}$ is
(a) H,
(b) $C_{1-6}$ alkyl, or mono or disubstituted $C_{1-6}$ alkyl, wherein the substitutents independently selected from the group consisting of phenyl, unsubstituted or substituted with —OH, $C_{1-3}$ alkyl, —CN, halogeno, —$CF_3$ or $C_{1-3}$ alkoxy; —OH; =O; —CN; halogeno; and —$CF_3$;
(c) phenyl, naphthyl, or mono, di or trisubstituted phenyl or naphthyl, wherein the substitutents are independently selected from the group consisting of —OH, $C_{1-3}$ alkyl, —CN, halogeno and —$CF_3$; and
(d) $C_{1-3}$ alkyloxy; or $R^{41}$ and $R^{42}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —$CF_3$;

J is carbon and $R^{43}$, $R^{44}$, $R^{45}$ and $R^{46}$ are independently selected from the group consisting of H, —OH, =O, —$NR^{47}R^{48}$ or —$NR^{47}C(O)$—$NR^{47}R^{48}$, wherein the nitrogen of —$NR^{47}R^{48}$ is optionally quaternized with $C_{1-4}$ alkyl or phenyl-$C_{1-4}$ alkyl or is optionally present as the Noxide; or $R^{43}$ and $R^{44}$, or $R^{44}$ and $R^{45}$, together form a carbon-carbon bond; or $R^{43}$ and $R^{44}$ or $R^{44}$ and $R^{45}$, or $R^{45}$ and $R^{46}$, together with the carbons to which they are attached form an aryl or heteroaryl ring, wherein heteroaryl is as defined above, and wherein the aryl or heteroaryl group is unsubstituted, mono, di or tri substituted, wherein the substitutents are independently selected from the group consisting of:
(a) $C_{1-6}$ alkyl, branched or unbranched, unsubstituted or mono or disubstituted by hydroxy (b) =O
(c) OR$^{47}$
(d) halogeno
(e) CF$_3$
(f) NO$_2$
(g) CN
(h) NR$^{47}$R$^{48}$
(i) NR$^{47}$COR$^{48}$
(O) NR$^{47}$CO$_2$R$^{48}$
(k) NR$^{47}$S(O)$_j$R$^{48}$
(l) CONR$^{47}$R$^{48}$
(m) COR$^{47}$
(n) CO$_2$R$^{47}$
(o) S(O)$_k$R$^{47}$
(p) heteroaryl, or mono or di substituted heteroaryl, wherein heteroaryl is as defined above and the substituents are selected from the group consisting of: C$_{1-6}$ alkyl, branched or unbranched, unsubstituted or mono or disubstituted by OH; =O; OR$^{47}$; CF$_3$; —NO$_2$; CN; NR$^{47}$R$^{48}$; NR$^{47}$COR$^{48}$; NR$^{47}$CO$_2$R$^{48}$; NR$^{47}$S(O)$_j$R$^{48}$; CONR$^{47}$R$^{48}$; COR$^{47}$; CO$_2$R$^{47}$; S(O)$_j$R$^{47}$; and phenyl; or R$^{43}$, R$^{44}$ and R$^{45}$ are as defined above and J-R$^{46}$ is oxygen or S(O)$_j$, wherein i is 0, 1, or 2; and R$^{47}$, R$^{47'}$ and R$^{48}$ are independently selected from the group consisting of:
(a) H,
(b) C$_{1-6}$ alkyl, or mono or disubstituted C$_{1-6}$ alkyl, wherein the substituents independently selected from the group consisting of phenyl, —OH, =O, —CN, halogeno and —CF$_3$;
(c) phenyl, naphthyl, or mono, di or trisubstituted phenyl or naphthyl, wherein the substituents are independently selected from the group consisting of —OH, C$_{1-3}$ alkyl, —CN, halogeno and —CF$_3$; and
(d) C$_{1-3}$ alkyloxy; or R$^{47}$ and R$^{48}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —CF$_3$.

Preferred are compounds of formula I wherein X is —O—, —C(O)—, a bond, —NR$^6$—, —S(O)$_e$—, —N(R$^6$)C(O)—, —OC(O)NR$^6$ or —C(=NOR$^1$)—. More preferred are compounds of formula I wherein X is —O—, —NR$^6$—, —N(R$^6$)C(O)— or —OC(O)NR$^6$. Additional preferred definitions are: b is 1 or 2 when X is —O— or —N(R$^6$)—; b is 0 when X is —N(R$^6$)C(O)—; and d is 1 or 2. T is preferably R$^4$-aryl, R$^4$-heteroaryl, R$^4$-cycloalkyl or R$^{10}$-bridged cycloalkyl, with R$^4$-aryl, especially R$^4$-phenyl, being more preferred. Also preferred are compounds wherein R$^{6a}$, R$^{7a}$, R$^{8a}$ and R$^{9a}$ are independently hydrogen, hydroxyalkyl or alkoxyalkyl, with hydrogen being more preferred. Especially preferred are compounds wherein R$^{8a}$ and R$^{9a}$ are each hydrogen, d and b are each 1, X is —O—, —NR$^6$—, —N(R$^6$)C(O)— or —OC(O)NR$^6$, T is R$^4$-aryl and R$^4$ is two substituents selected from C$_1$–C$_6$ alkyl, halogeno, —CF$_3$ and C$_1$–C$_6$ alkoxy. Preferred definitions for T being R$^4$-heteroaryl include R$^4$-quinolinyl and oxadiazolyl.

Also preferred are compounds of formula I wherein R is hydrogen. Q is preferably R$^5$-phenyl, R$_5$-naphthyl or R$^5$-heteroaryl; an especially preferred definitions for Q are R$^5$-phenyl, wherein R$^5$ is preferably two halogeno substituents, and R$^5$-heteroary, especially R$^5$-benzothienyl wherein R$^5$ is preferably H.

Preferred are compounds of formula I wherein A is =N—OR$^1$ or =N—N(R$^2$)(R$^3$). More preferred are compounds wherein A is =N—OR$^1$. R$^1$ is preferably H, alkyl, —(CH$_2$)$_n$—G, —(CH$_2$)$_p$—M—(CH$_2$)$_n$—G or —C(O)N(R$^6$)(R$^7$), wherein M is —O— or —C(O)N(R$^9$)— and G is —CO$_2$R$^6$, —OR$^6$, —C(O)N(R$^6$)(R$^9$), —C(=NOR$^8$)N(R$^6$)(R$^7$), —C(O)N(R$^9$)(R$^4$-heteroaryl) or R$^4$- heteroaryl. R$^2$ and R$^3$ are independently preferably H, C$_1$–C$_6$ alkyl, —(C(R$^6$)(R$^7$))$_n$—G or G$^2$.

Preferred definitions of Z having the spirocyclic structure

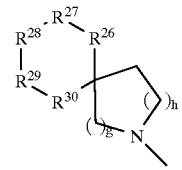

are exemplified by the following structures, optionally substituted at the positions indicated by numbers 1–8 with —OH, =O, —CN, —NR$^{35}$R$^{36}$, —NHCOR$^{35}$R$^{36}$, halogeno, —CF$_3$, phenyl, mono, di or trisubstituted phenyl, wherein the phenyl substituents are independently selected from the group of substituents defined immediately above and C$_{1-3}$ alkyl:

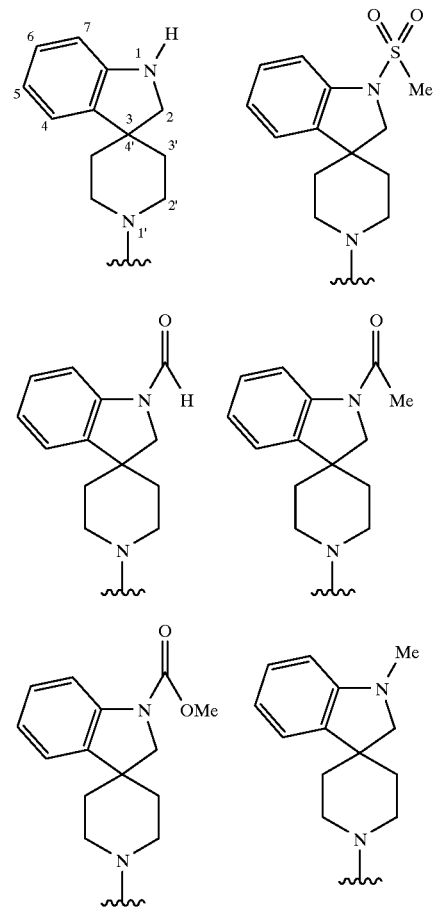

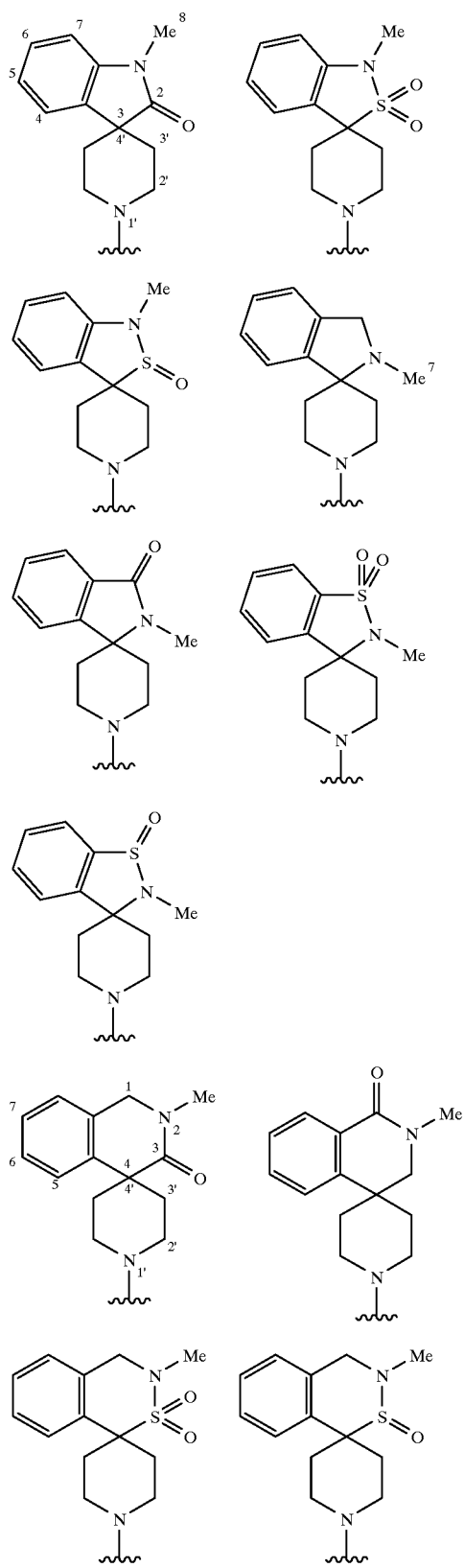
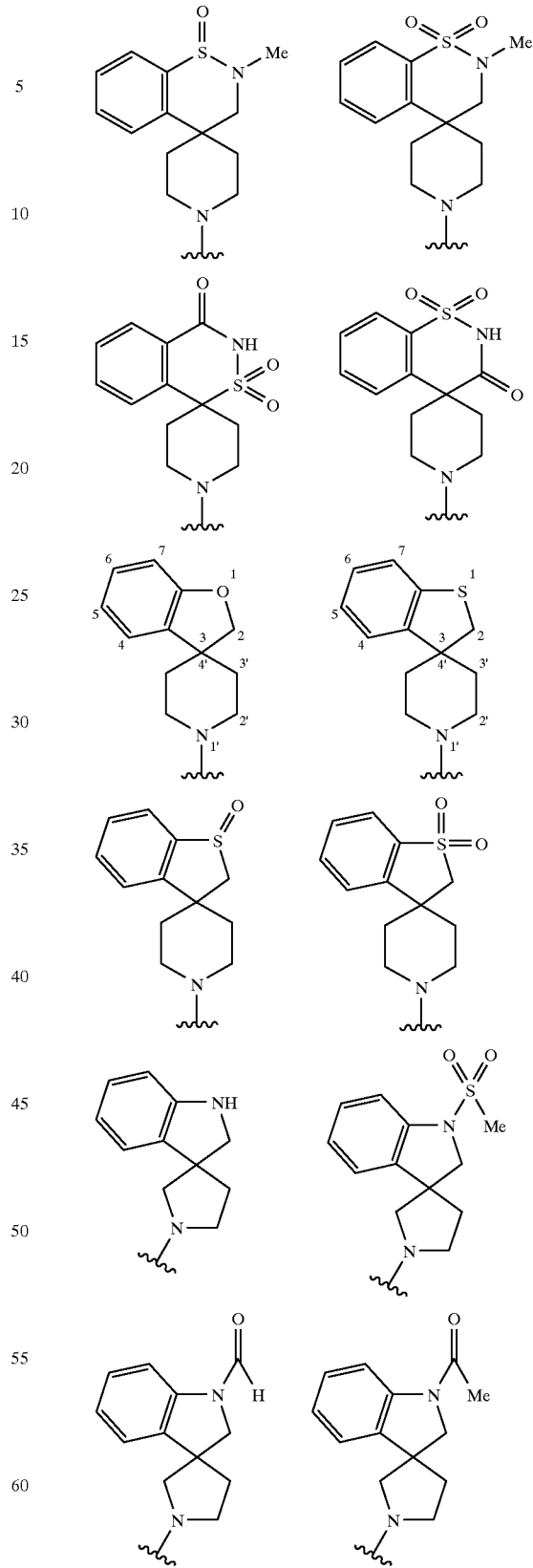

-continued
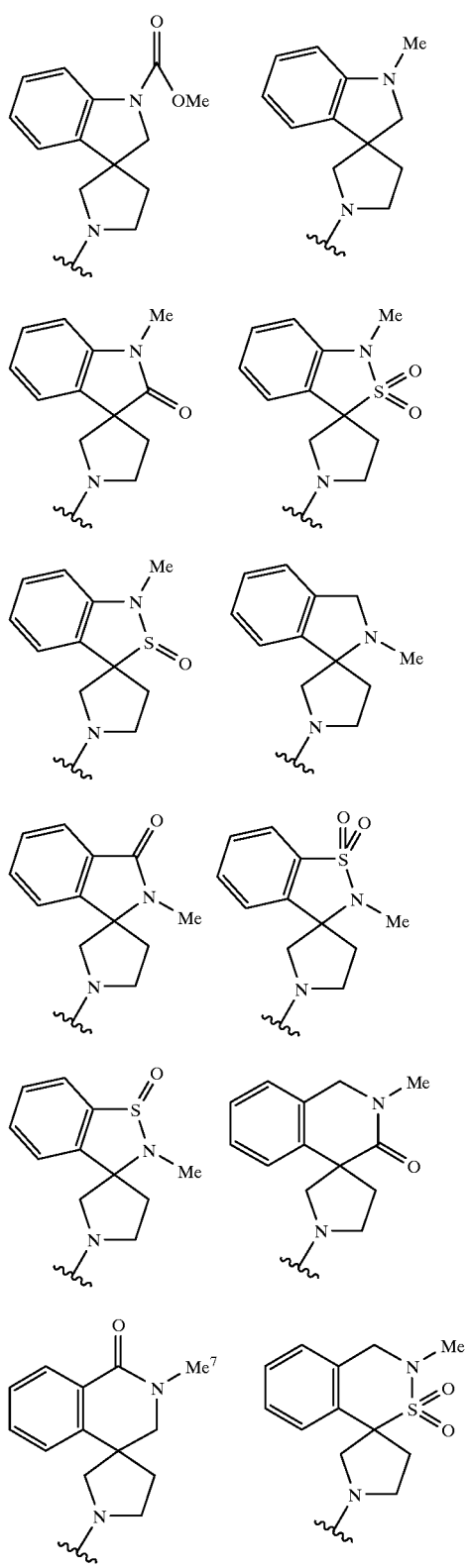
-continued
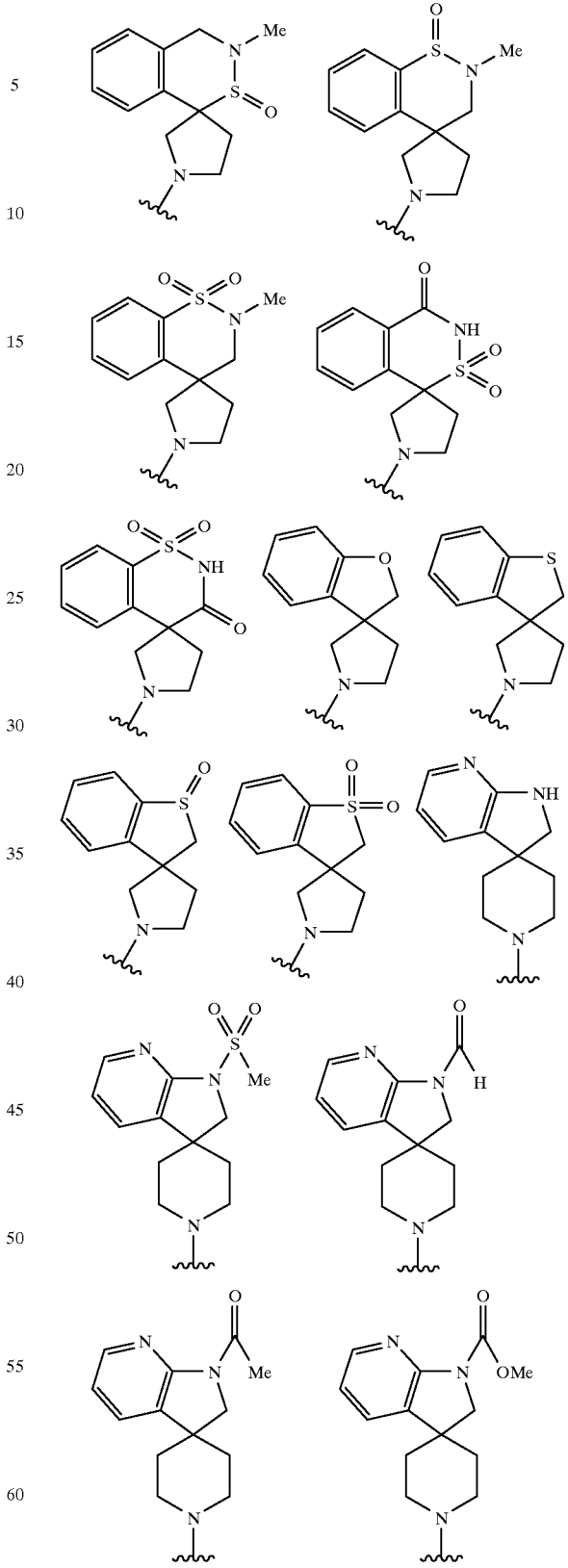

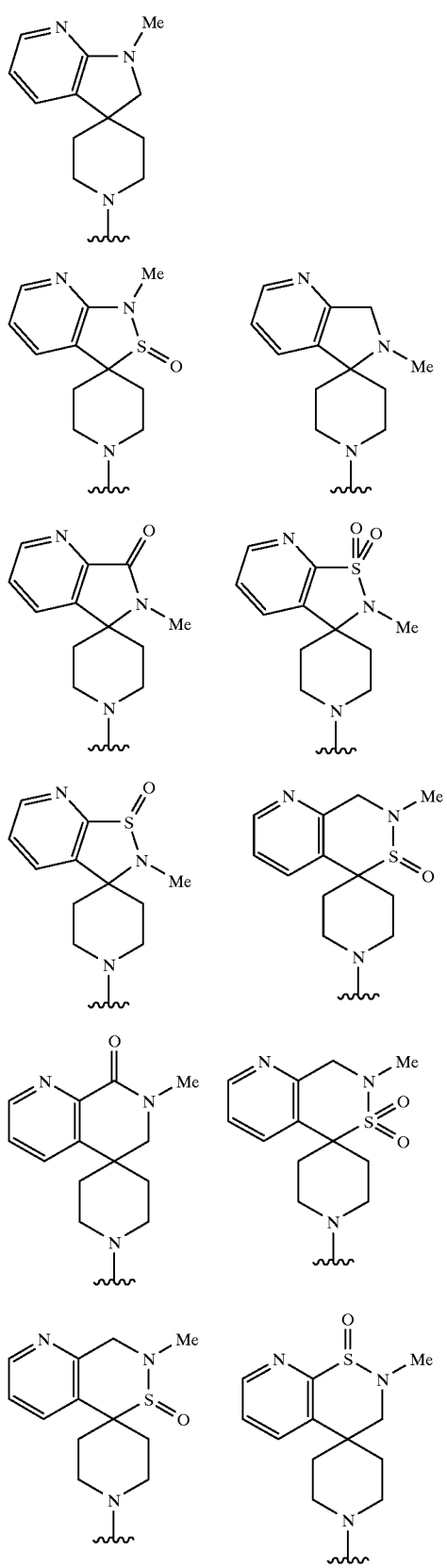
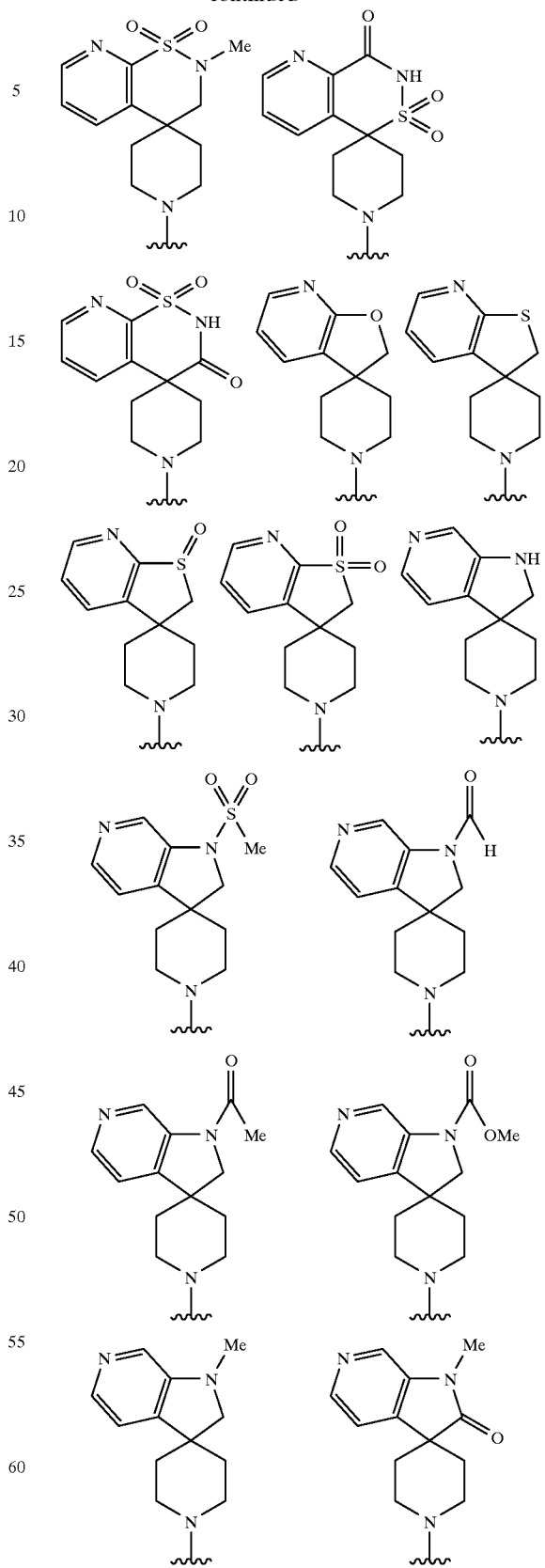

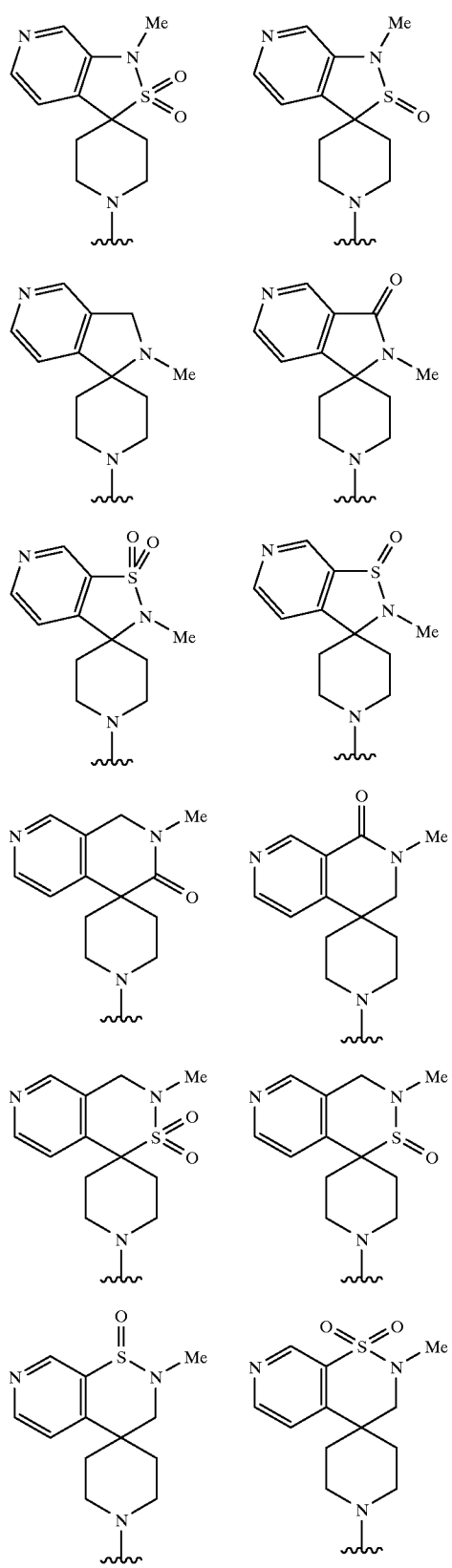
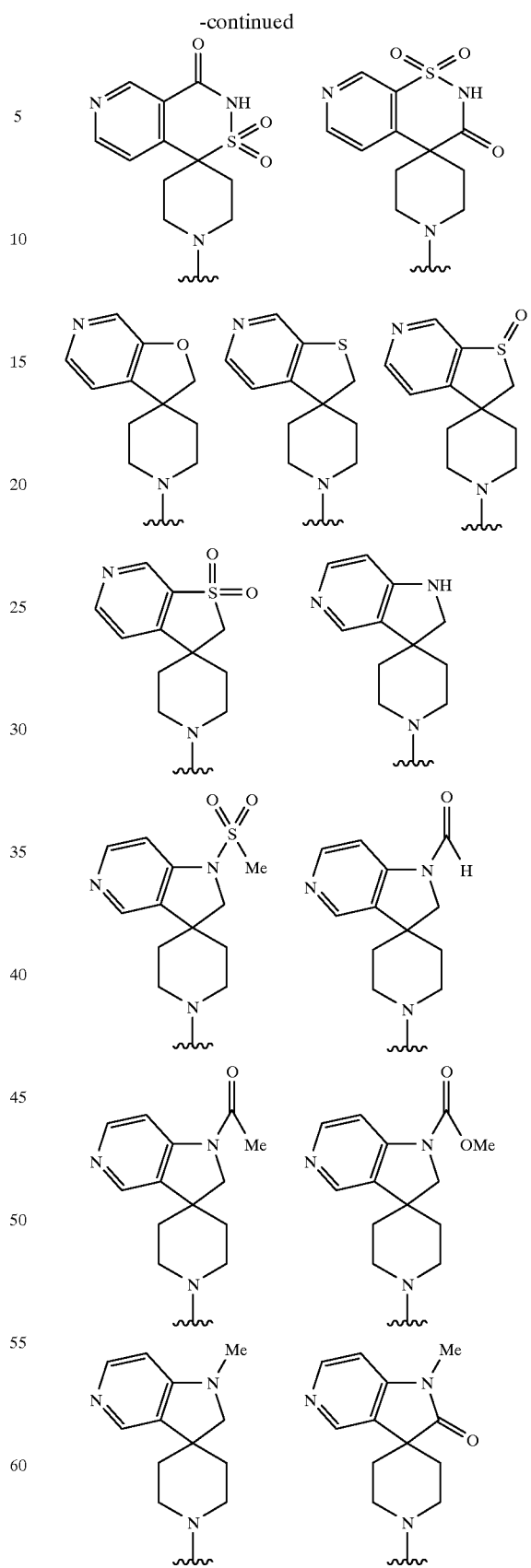

-continued
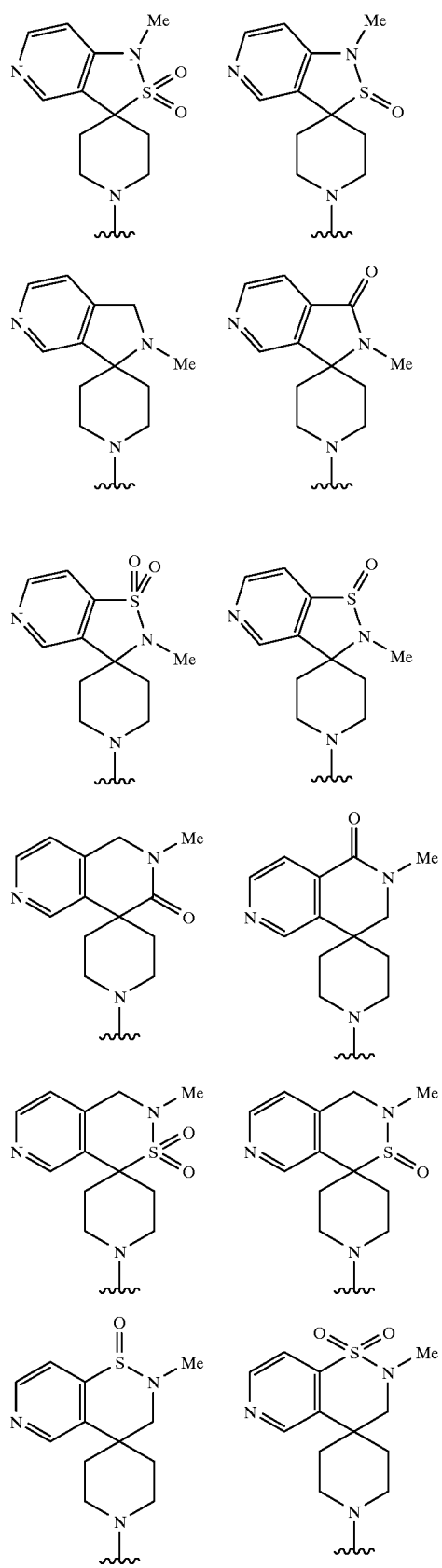
-continued
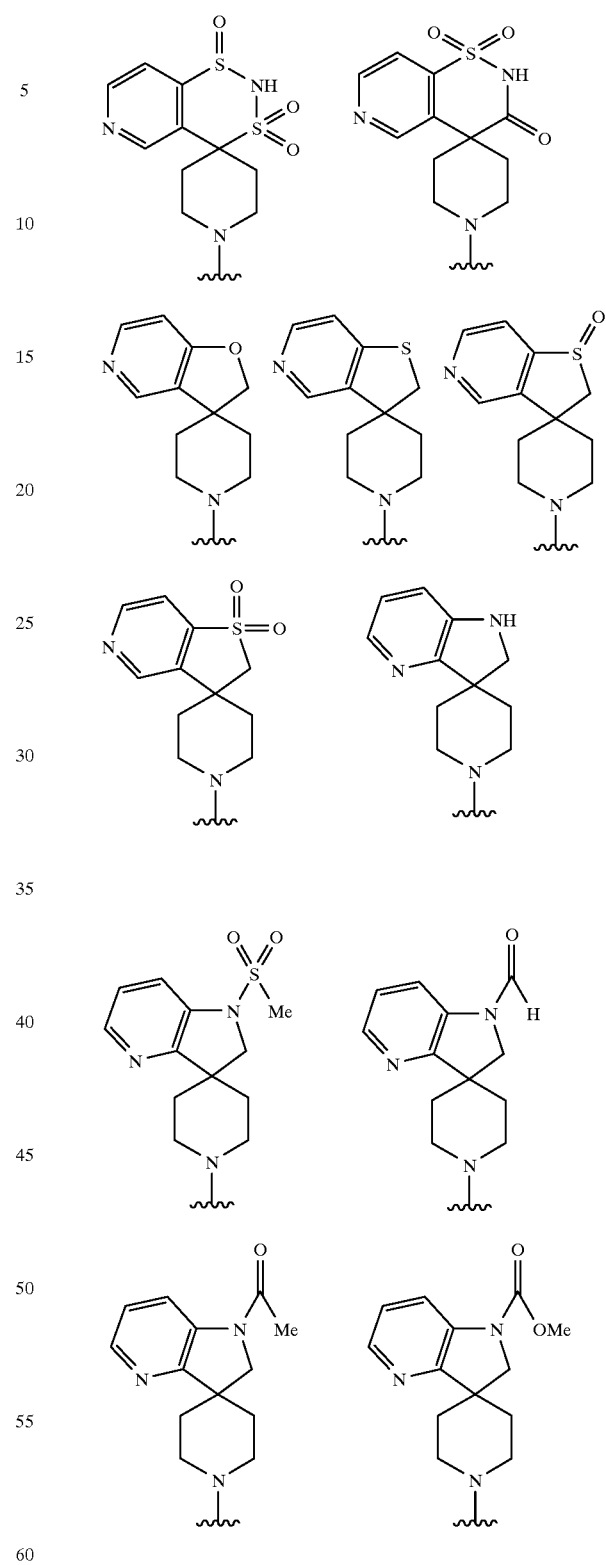

-continued
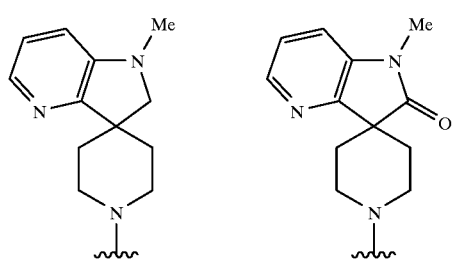 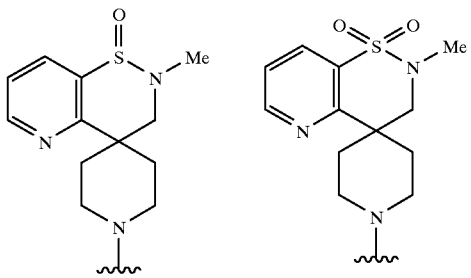
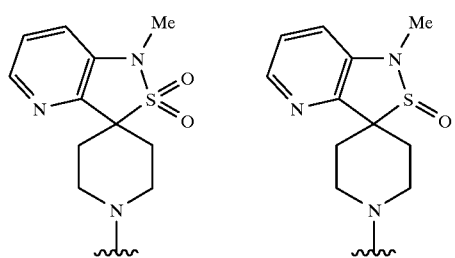 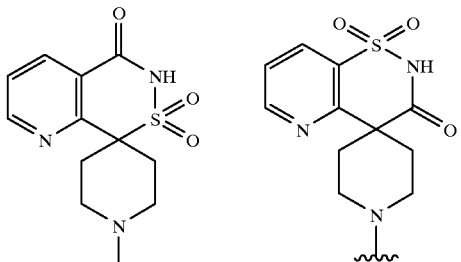
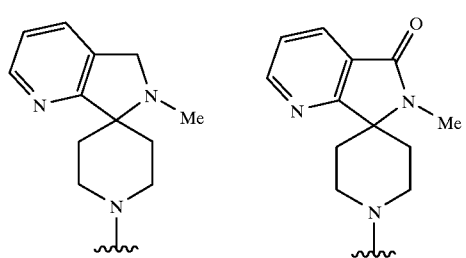 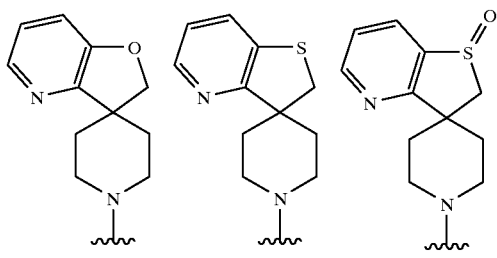
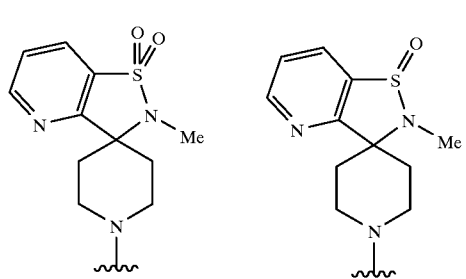 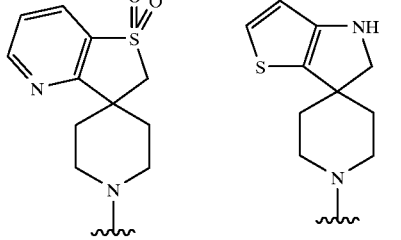
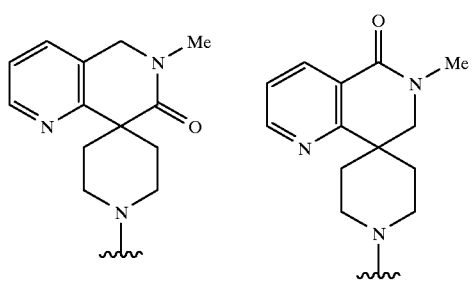 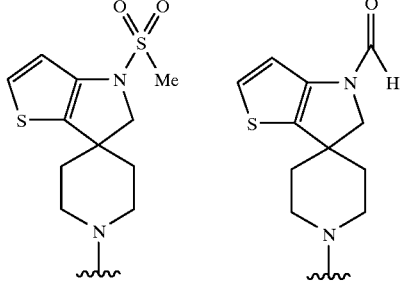
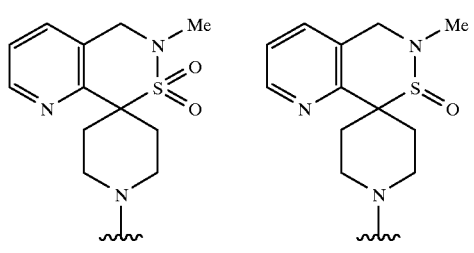 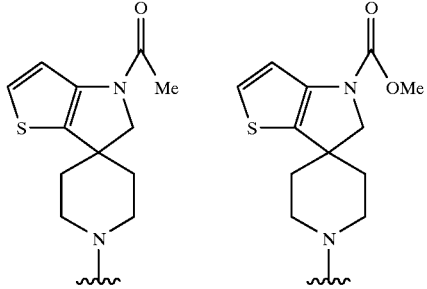

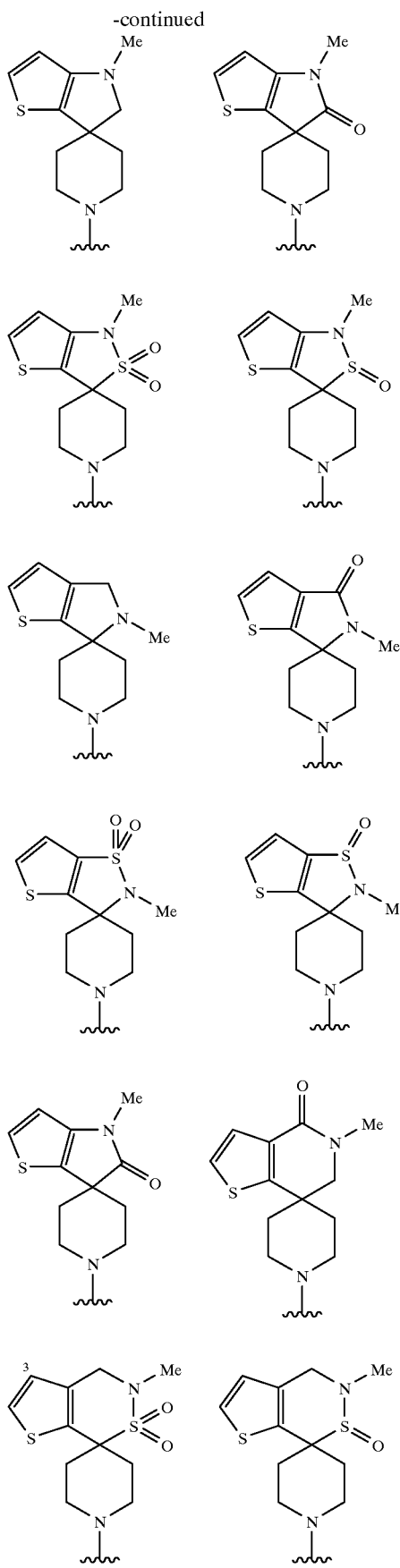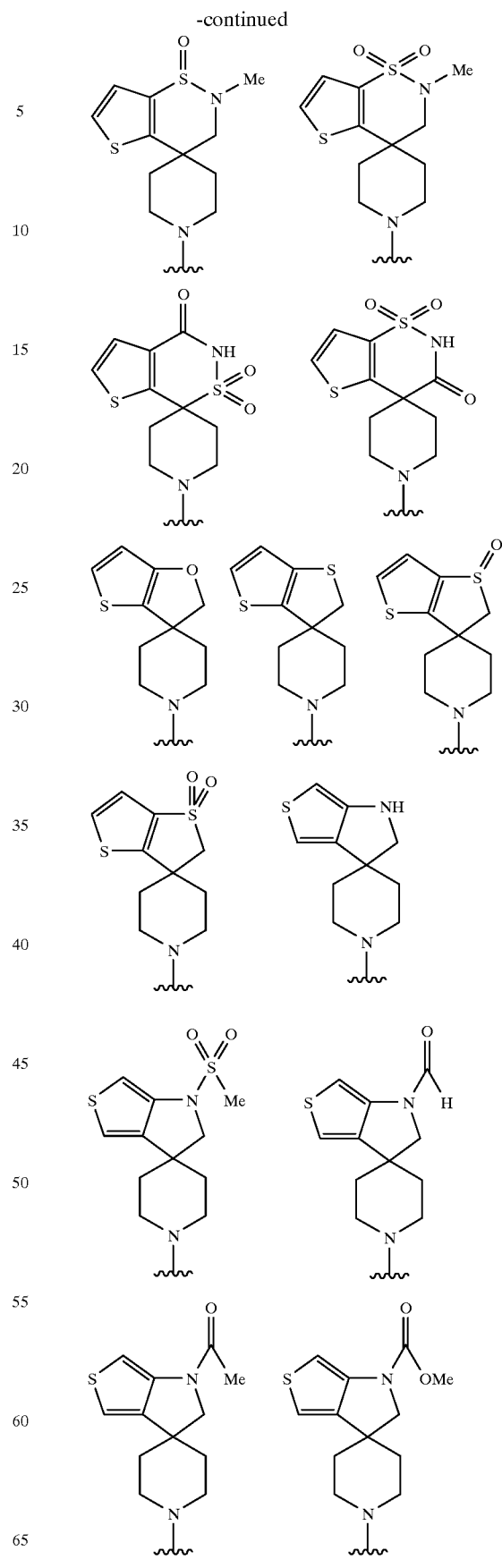

-continued
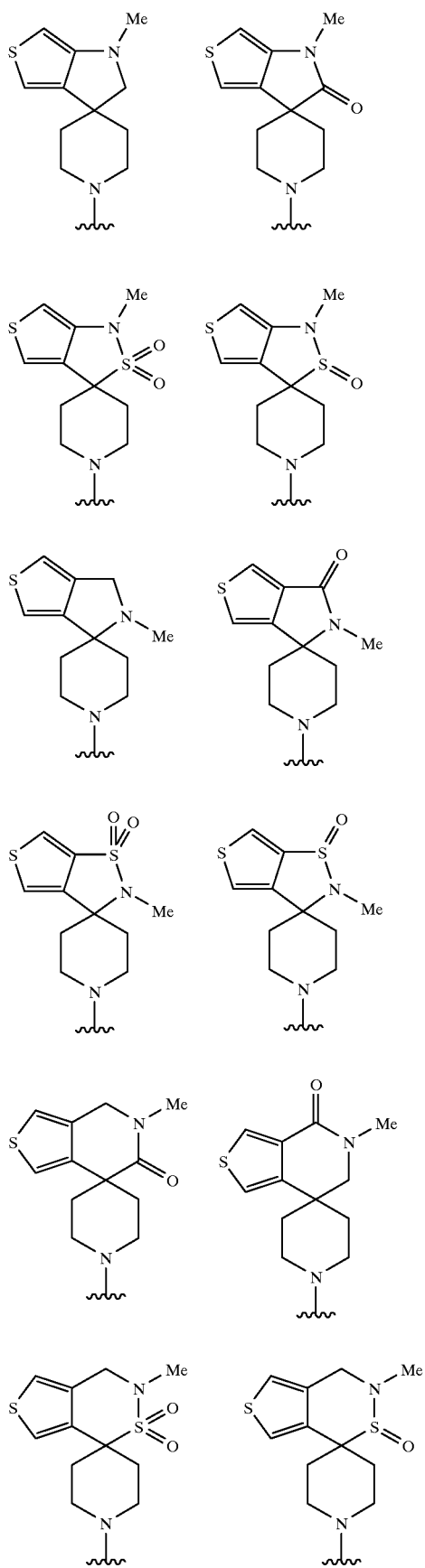
-continued
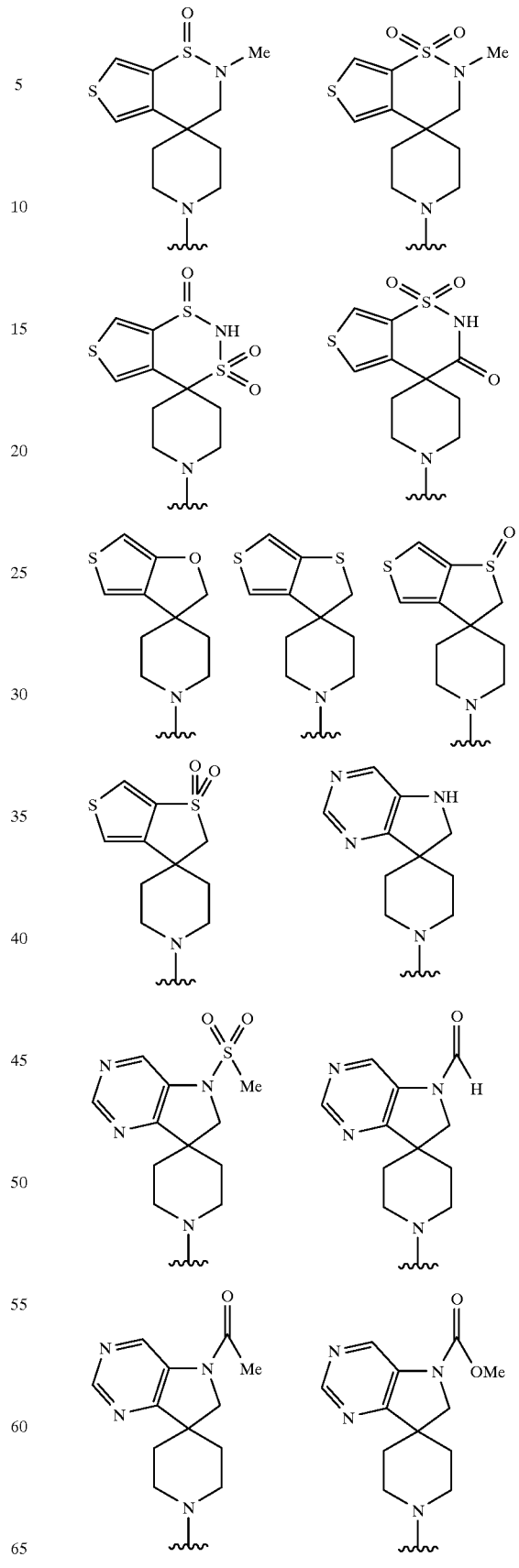

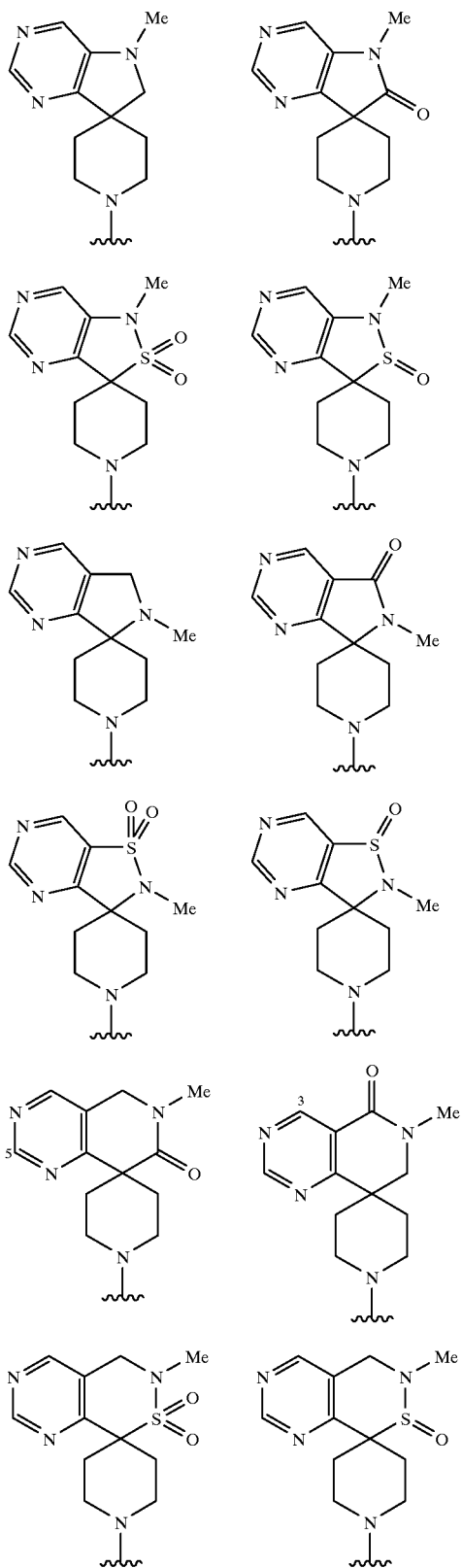
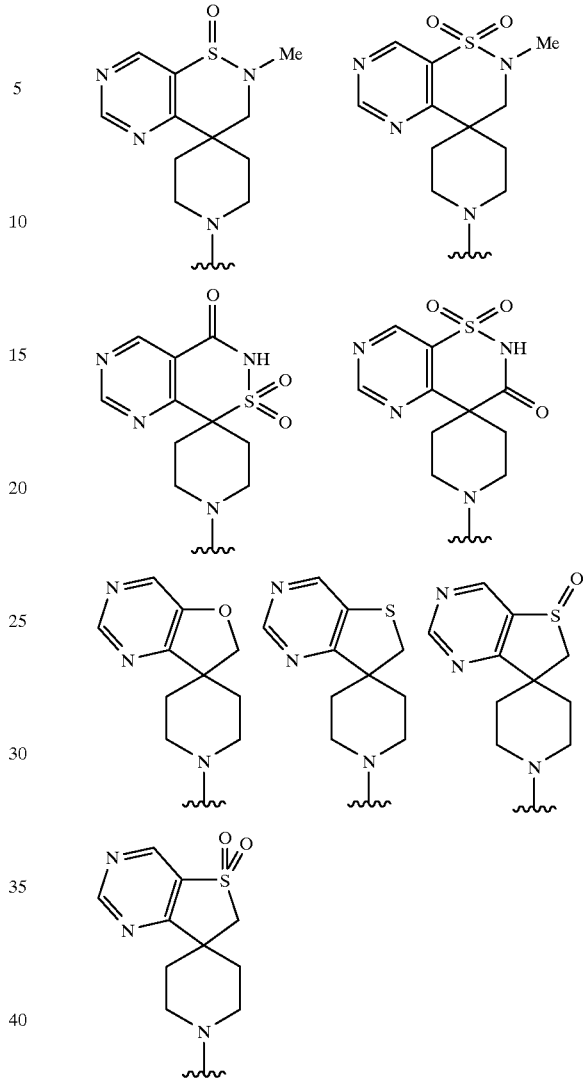

Preferred definitions of Z having the substituted aryl piperazinyl structure are those wherein $R^{39}$ is H and Ar is selected from the group consisting of phenyl, pyrazinyl, pyrazolyl, pyridyl, pyrimidyl and thienyl, wherein the Ar group is mono- or d-substituted with $C_{1-3}$ alkyl, =O, —$OR^{41}$, halogen, —$CF_3$, —$CONR^{41}$—($C_{1-2}$ alkyl), —$CO_2H$, —$CO_2$—($C_{1-2}$ alkyl), —$CH_2NR^{41}$—($C_{1-2}$ alkyl), —$CH_2NH$—C(O)—($C_{1-3}$ alkyl), —$CH_2NH$—C(O)$NH_2$, —$CH_2NH$—C(O)NH—($C_{1-3}$ alkyl), —$CH_2NH$—C(O)N— (di-$C_{1-3}$ alkyl), —$CH_2NH$—S(O)$_j$—($C_{1-3}$ alkyl) or —$CH_2$-heteroaryl, wherein heteroaryl is imidazolyl, oxazolyl, pyridyl, tetrazolyl or triazolyl, and wherein the heteroaryl is optionally substituted with branched or unbranched, optionally hydroxy-substituted $C_{1-6}$ alkyl. More preferred are compounds wherein Ar is mono- or d-substituted phenyl wherein the substituents are $C_{1-3}$ alkyl, =O, —$OR^{41}$, —$CONR^{41}$—($C_{1-2}$ alkyl), —$CH_2NR^{41}$—($C_{1-2}$ alkyl), —$CH_2NH$—C(O)—($C_{1-3}$ alkyl), —$CH_2NH$—C(O)$NH_2$, —$CH_2NH$—C(O)NH—($C_{1-3}$ alkyl), —$CH_2NH$—C(O)N— (di-$C_{1-3}$ alkyl), —$CH_2NH$—S(O)$_j$—($C_{1-3}$ alkyl) or —$CH_2$-heteroaryl, wherein heteroaryl is as defined immediately above. Typical groups Ar groups wherein Z is a substituted aryl piperazinyl are shown in the following formulae:
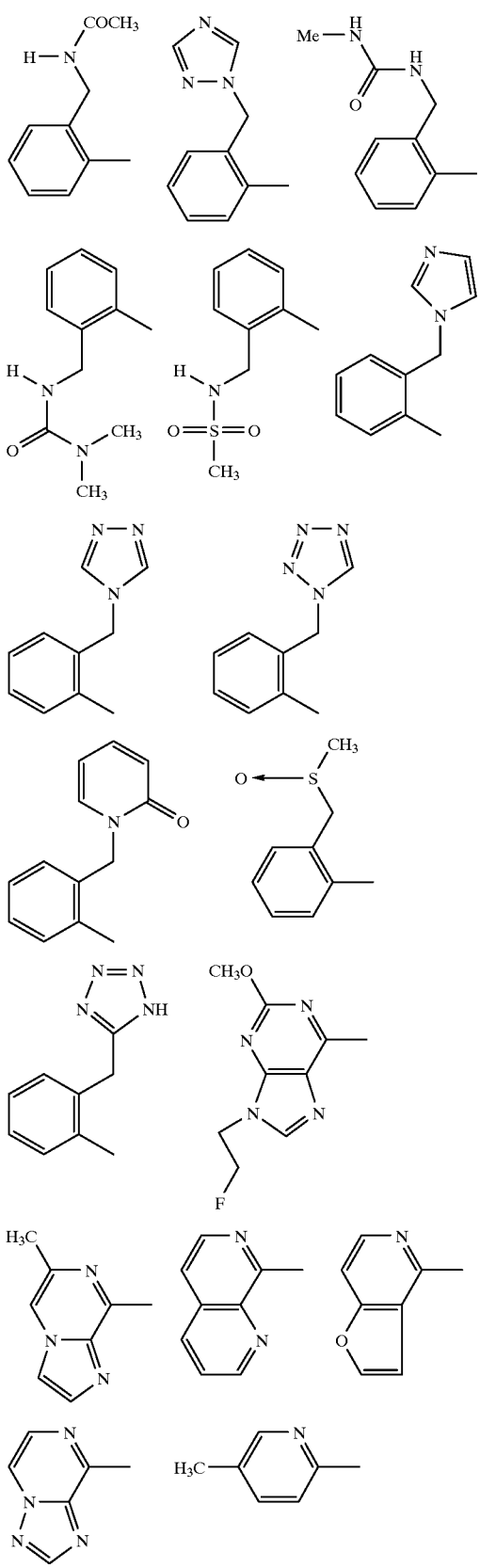
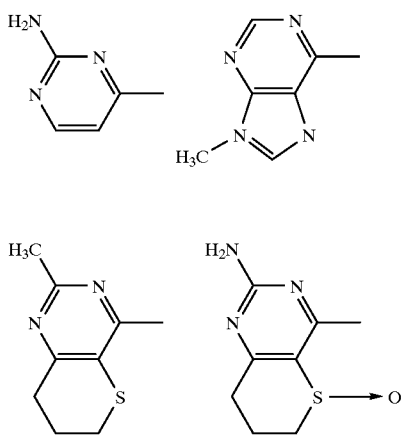
Preferred definitions of Z having the spirocyclic structure
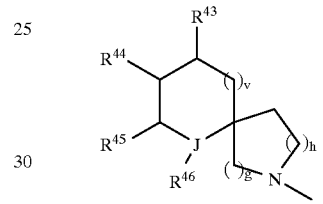
are exemplified by the following structures,
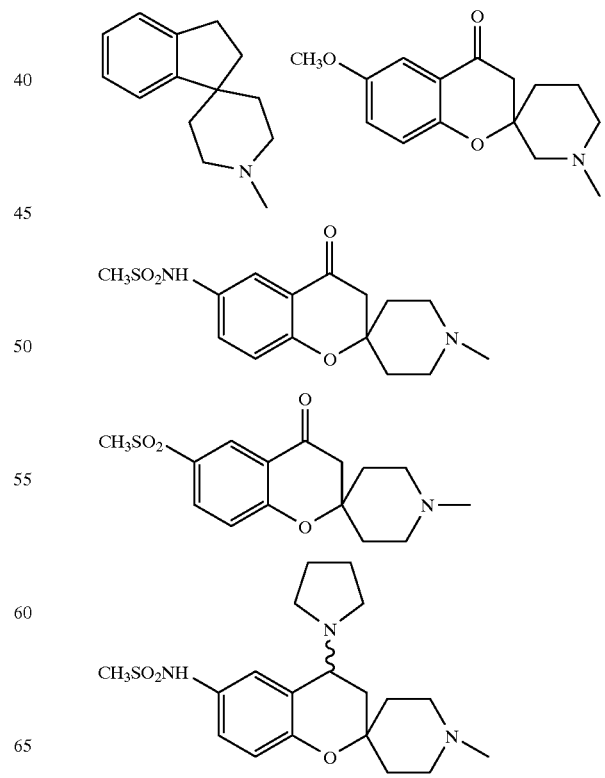

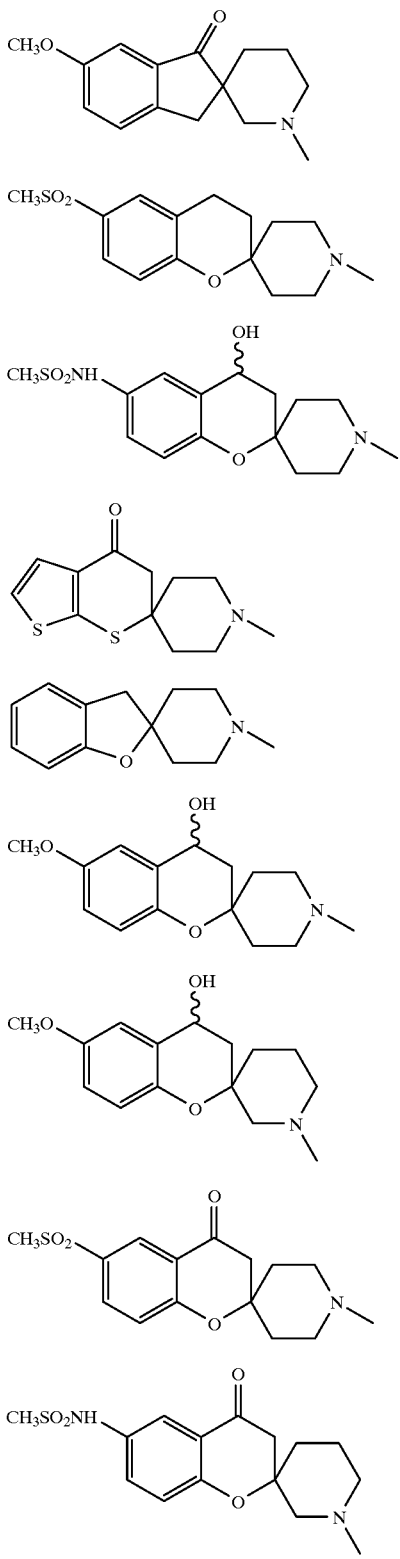
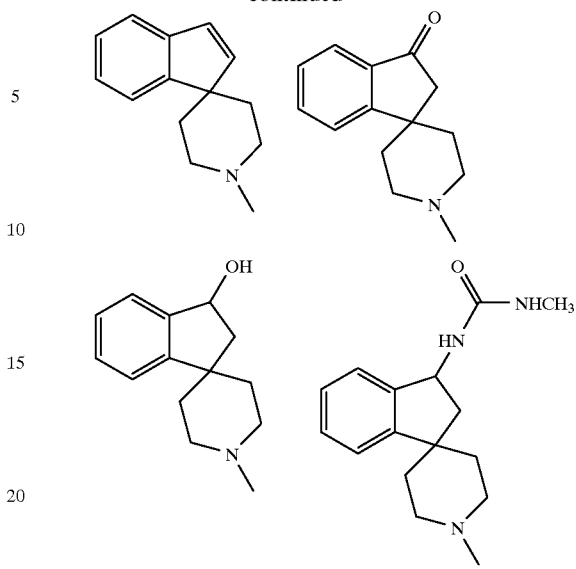

This invention also relates to the use of a compound of formula I in the treatment of asthma, cough, bronchospasm, inflammatory diseases such as arthritis, central nervous system conditions such as migraine and epilepsy, nociception, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, bronchospasm, inflammatory diseases such as arthritis, migraine, nociception, and various gastrointestinal disorders such as Crohn's disease.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 6 carbon atoms. "Bridged cycloalkyl" refers to $C_7$–$C_{10}$ saturated rings comprised of a cycloalkyl ring or a fused bicycloalkyl ring and an alkylene chain joined at each end to non-adjacent carbon atoms of the ring or rings. Examples of such bridged bicycloalkyl rings are adamantyl, myrtanyl, noradamantyl, norbornyl, bicyclo[2.2.1]heptyl, 6,6-dimethylbicyclo[3.1.1]heptyl, bicyclo[3.2.1]octyl, and bicyclo[2.2.2]octyl.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N($R^{19}$)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, isoxazolyl, oxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, thianaphthenyl (i.e., benzothienyl) benzimidazolyl, benzoxazolyl, and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Where $R^2$ and $R^3$ or $R^6$ and $R^7$ substituents on a nitrogen atom form a ring and additional heteroatoms are present, the rings do not include adjacent oxygen and/or sulfur atoms or three adjacent heteroatoms. Typical rings so formed are morpholinyl, piperazinyl and piperidinyl.

In the above definitions, wherein variables $R^6$, $R^7$, $R^8$, $R^9$, $R^{10}$, $R^{13}$, $R^{14}$ and $R^{15}$, for example, are said to be independently selected from a group of substituents, we mean that $R^6$, $R^7$, $R^8$, $R^9$, $R^{10}$, $R^{13}$, $R^{14}$ and $R^{15}$ are independently selected, but also that where an $R^6$, $R^7$, $R^8$, $R^9$, $R^{10}$, $R^{13}$, $R^{14}$ or $R^{15}$ variable occurs more than once in a molecule, those occurrences are independently selected (e.g., if R is —$OR^6$— wherein $R^6$ is hydrogen, X can be —$N(R^6)$— wherein $R^6$ is ethyl). Similarly, $R^4$ and $R^5$ can be independently selected from a group of substituents, and where more than one $R^4$ and $R^5$ are present, the substitutents are independently selected; those skilled in the art will recognize that the size and nature of the substituent(s) will affect the number of substituents which can be present.

Compounds of formula I can have at least one asymmetrical carbon atom and all isomers, including diastereomers, enantiomers and rotational isomers, as well as E and Z isomers of the oxime, hydrazone and olefin groups, are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art. Following are typical procedures for preparing various compounds; the skilled artisan will recognize that other procedures may be applicable, and that the procedures may be suitably modified to prepare other compounds within the scope of formula I.

Procedure A

Compounds of formula I wherein R is H, a and d are each 1, X is —O— or —S— and the remaining variables are as defined above (Q is exemplified as $R^5$-phenyl, but the procedure is not limited to this definition) can be prepared according to the following reaction scheme:

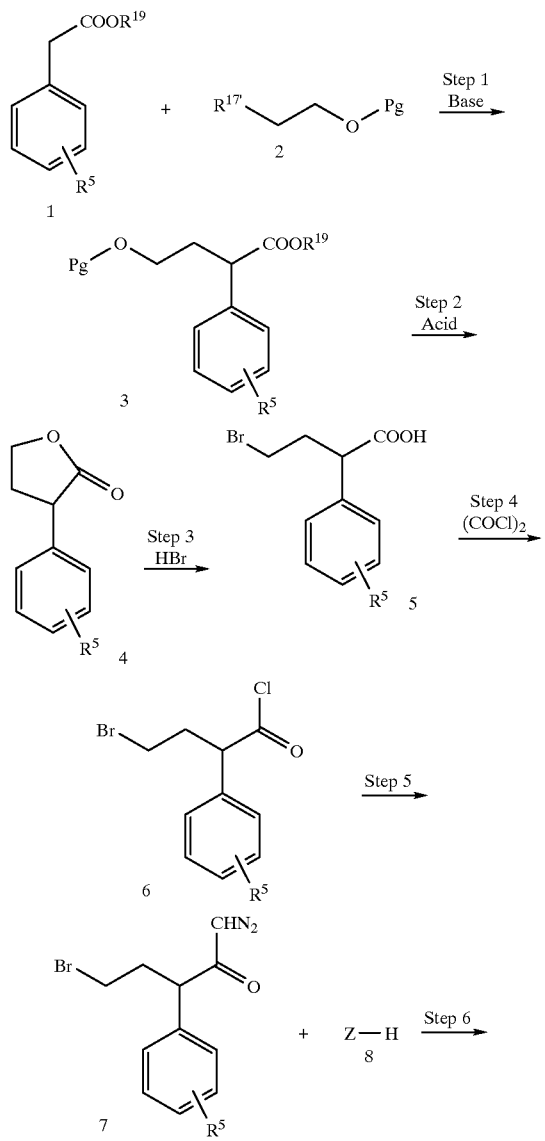

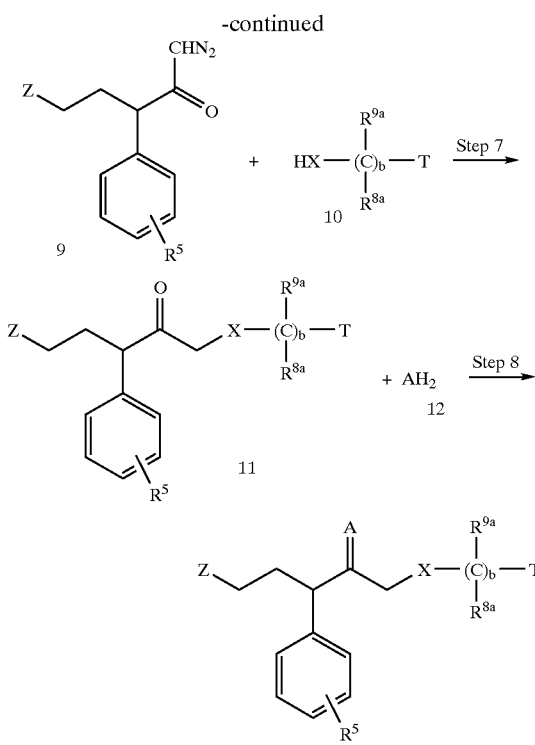

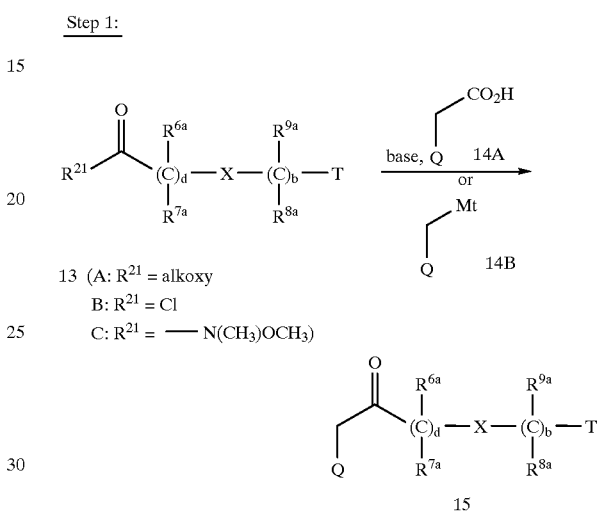

In step 1, the ester (preferably methyl) of the substituted aryl acetic acid of formula 1, wherein $R^{19}$ is a lower alkyl group, preferably methyl, is reacted with a compound of formula 2, wherein $R^{17'}$ is a leaving group such as Br, I or triflate, and Pg is a suitable protecting group such as tetrahydropyranyl, and a base to prepare a compound of formula 3. The base can be chosen from any strong base including LDA or lithium bis(trimethylsilyl)amide. The reaction is carried out in an inert organic solvent such as THF at temperatures of −15 to about 65° C.

In step 2, a compound of formula 3 is reacted with an acid in a solvent such as $CH_3OH$, at temperatures ranging from −10 to 65 °C. The acid need not to be used in stochiometric amount. Alternatively, a compound of formula 4 can be prepared directly from step 1 without isolating the compound of formula 3: the reaction mixture obtained after the work up of the reaction described in step 1 can be dissolved in the solvent and reacted with the acid.

In step 3, a compound of formula 4 is reacted with an acid such hydrobromic acid (HBr) dissolved in a suitable solvent such as acetic acid. The reaction is performed at temperatures ranging from 5 to 45° C.

In step 4, the carboxylic acid of formula 5 is reacted with a halogenating agent such as $SOCl_2$ or $(COCl)_2$ in an appropriate solvent such $CH_2Cl_2$ to form the acid halide of formula 6.

In step 5, the compound of formula 6 is reacted with an alkylating agent such as diazomethane to obtain the compound of formula 7. This reaction may be performed at temperatures lower than ambient using an appropriate solvent such as $Et_2O$.

In step 6, a compound of formula 7 is reacted with a compound of formula 6 to obtain a compound of formula 9. The reaction is carried out in a suitable solvent, e.g. EtOAc, at temperatures below 85° C. Bases such as $Et_3N$ may be beneficial to the reaction.

In step 7, a compound of formula 9 is reacted with a compound of formula 10, wherein X is —O— or —S—, T is H, $R^4$-aryl, $R^4$-cycloalkyl, $R^4$-alkyl, $R^4$-bicyclo or tricycloalkyl, and $R^{8a}$, $R^{9a}$, b and $R^4$ are as defined above in an appropriate solvent, e.g. $CH_2Cl_2$, with a Lewis acid, e.g. $BF_3$, at temperatures lower than 50° C.

In step 8 a compound of formula 11 is reacted with a compound of formula 12, wherein A is as defined above, in a solvent such as pyridine, to obtain the desired product.

Procedure B

Compounds of formula I, wherein the variables are as defined above, can be prepared as shown in the following reaction scheme:

Step 1:

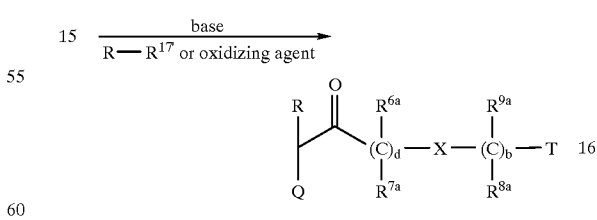

In step 1, a compound of formula 14A, wherein Q is as defined above, is reacted with a base such as lithium disopropylamide (LDA) or KH in an inert organic solvent such at THF or DME to generate a dianion. An acid chloride, ester or amide of formula 13A, 13B, or 13C is added to give a ketone of formula 15. Preferable reaction temperatures ranges from −78° C. to 30° C.

Alternatively, compounds of formula 15 can be generated by the reaction of a compound of formula 13, preferably 13C, with a metallated species of formula $QCH_2Mt$ where Mt is a metal, such as MgHal, wherein "Hal" is halogen, or lithium. The metallated species $QCH_2Mt$ can be generated by conventional procedures, such as treatment compounds of formula $QCH_2Hal$ with Mg or by treating $QCH_3$ with an organolithium base.

Step 2:

15 —base / R—$R^{17}$ or oxidizing agent→

[structure 16]

In step 2, for compounds of formula I wherein R is not hydrogen, the ketone 15 is reacted with a suitable base, such as LDA or KH in an inert organic solvent such as THF. For compounds wherein R is alkyl or hydroxyalkyl, a compound R-$R^{17'}$, wherein $R^{17'}$ (as defined above) is added. For compounds wherein R is OH, an appropriate oxidizing agent such as dimethyldioxirane or Davis reagent is added. Preferable reaction temperatures range from −78° to 50° C.

Step 3:

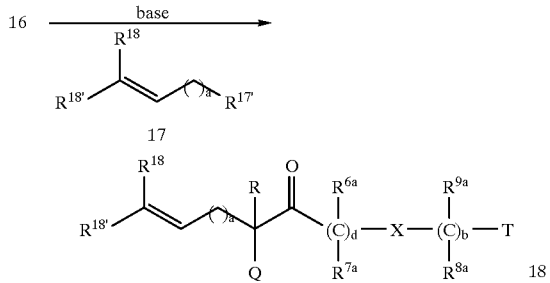

In step 3, ketone 16 is reacted with a base such as LDA in a solvent such as THF, then an olefin of formula 17 is added, wherein $R^{18}$ and $R^{18'}$ are independently H or lower alkyl and $R^{17'}$ is as defined above, to give the adduct 18. Preferable reaction temperatures range from −78 to 60° C.

Step 4:

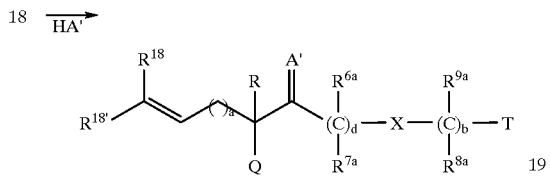

In step 4, ketone 18 is reacted with HA', wherein A' is NH—$OR^1$, NH—N($R^2$)($R^3$) or $NHR^{26}$, in an organic solvent such as pyridine at a temperature from 25° C. to 150° C. to give a compound of formula 19.

Step 5:

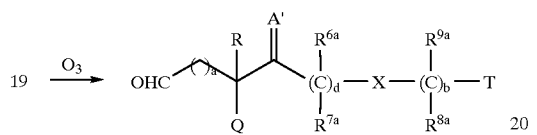

In step 5, a compound of formula 19 is oxidized by ozonolysis to give an aldehyde of formula 20. Suitable organic solvents include EtOAc, ethanol or the like. Preferable reaction temperatures are from −78 to 0° C.

Step 6:

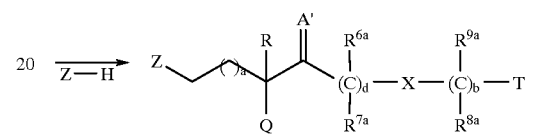

In step 6, an aldehyde of formula 20 is reacted with a compound of formula Z-H, wherein Z is a suitably substituted amine (as its acid salt e.g. HCl or maleate or as its free base) and a hydride source such as —$NaBH_3CN$ or sodium triacetoxyborohydride in a protic solvent (e.g. $CH_3OH$, $CH_3CH_2OH$, or $CF_3CH_2OH$) with 3A sieves. Any suitable temperature can be used with preferable temperatures being between 0° C. and 25° C.

Alternatively, a compound of formula I can be prepared from 18 by the following reaction scheme:

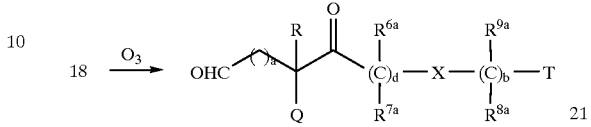

Compound 18 is oxized to a compound of formula 21 under conditions similar to those described for step 5 above. The aldehyde of formula 21 is reacted with a compound of formula Z-H in a manner similar to that described in Step 6, and the resultant ketone is then reacted with a compound of the formula HA' as described above in Step 4 to obtain the compound of formula I.

Procedure C

Step 1:

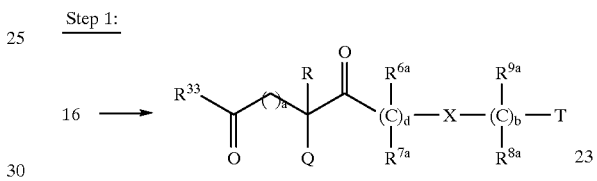

In step 1, compounds of formula 16 treated with an appropriate base, such as NaH, are reacted with alkylating agents of the formula $R^{33}C(O)CH_2R^{17}$ or $R^{33}C(O)CH=CH_2$ wherein $R^{33}$ is alkoxy or —$N(CH_3)OCH_3$ and $R^{17}$ is a leaving group such as Cl or Br.

Step 2:

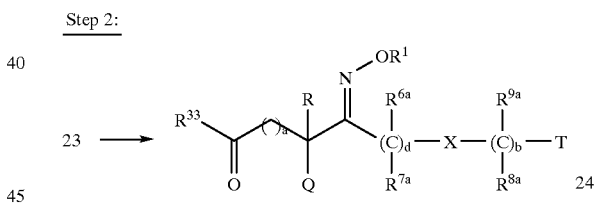

In step 2, compounds of formula 23 can be converted to the corresponding oxime of formula 24 in a manner similar to that described in Procedure B, Step 4.

Step 3:

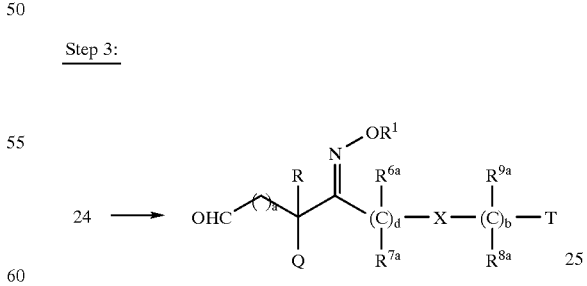

In step 3, compounds of formula 24 (or 23, i.e., wherein A' is O) are converted to the corresponding aldehyde 25 (or lactol from the keto-ester 23) by treatment with a suitable reducing agent such a DIBAL, in an suitable inert organic solvent such as THF, at a temperature from about −100 to −20° C.

Step 4:

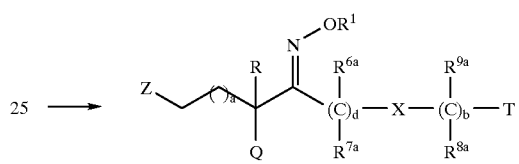

In step 4, compound 25 is reacted with an amine ZH in a manner similar to that described in Procedure B, Step 6, to obtain the compound of formula I.

Starting materials Z-H are known in the art or are prepared by methods known in the art, for example procedures for preparing spiro-substituted azacycles were described by Ong, et al, *J. Med. Chem.*, 26 (1983), p. 981–986 and in WO 94/29309, published Dec. 22, 1994;

substituted aryl piperazines were described in WO 96/10568, published Apr. 11, 1996.

In the above procedures, T and Q generally are exemplified as $R^5$-phenyl and $R^4$-phenyl, respectively, but those skilled in the art will recognize that in many cases, similar procedures can be used to prepare compounds wherein T and Q are other than substituted-phenyl.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \>NH | \>NCOalkyl, |
| | \>NCObenzyl, |
| | \>NCOphenyl, |
| | \>NCH₂OCH₂CH₂Si(CH₃)₃ |
| | \>NC(O)OC(CH₃)₃, |
| | \>N-benzyl, |
| | \>NSi(CH₃)₃, |

TABLE 1-continued

| Group to be Protected | Group to be Protected and Protecting Group |
|---|---|
| | \>NSi(CH₃)₂—C(CH₃)₃ |
| —NH₂ | (succinimide) |
| —OH | —OCH₃, —OCH₂OCH₃, —OSi(CH₃)₃, |
| | —OSi(CH₃)₂—C(CH₃)₃ |
| | or —OCH₂phenyl |

Compounds of formula I have been found to be antagonists of $NK_1$ and/or $NK_2$ and/or $NK_3$ receptors, and are therefore useful in treating conditions caused or aggravated by the activity of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution The pharmaceutical compositions can be prepared with conventional excipients and additives, using well known pharmaceutical formulation techniques.

Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I. As used herein, Me is methyl, Ac is acetyl, Et is ethyl and Ph is phenyl.

Preparation 1

1,2-Dihydro-1'-methyl-1-(methylsulfonyl)-spiro[3H-indole-3,4'-piperidine]

Dissolve 1,2-dihydro-1'-methyl-spiro[3H-indole-3,4'-piperidine] (3.0 g, 14.8 mmoles) in dry CH₂Cl₂ (25 ml) and cool under $N_2$ in an ice bath. Add, dropwise, methane sulfonyl chloride (1.5 ml, 19.3 mmoles), followed by ethyl diisopropyl amine (5.0 ml, 28.7 mmoles). Warm to room temperature and stir overnight. Dilute the solution to 100 ml with $CH_2Cl_2$. Wash the solution with saturated aqueous $NaHCO_3$ (4×25 ml), then with water. Dry solution with anhydrous $Na_2SO_4$, then remove the solvent using reduced pressure. Purify the resulting reaction mixture by flash chromatography ($SiO_2$) using 5% $MeOH(NH_3)$/EtOAc as eluent. Yield: 3.37 g (81%) of the title compound.

HRMS (FAR): calculated for $C_{14}H_{21}N_2O_2S$ $(M+H)^+$: 281.1324; found: 281.1324.

Preparation 2

1,2-Dihydro-1-(methylsulfonyl)-spiro[3H-indole-3,4'-piperidine]

Add 1-chloroethyl chlorocarbonate (1.0 ml, 9.3 mmoles) dropwise to a precooled (ice bath) solution of the product of Preparation 1 (2.0 g, 7.13 mmoles) in 1,2-dichloroethane (20 ml). After the addition, reflux the solution, under $N_2$, for 2 h. Cool the solution to room temperature and remove about half the volume of the solvent using reduced pressure. Add $CH_3OH$ (15.0 ml) and reflux the solution again for another 40 min. Remove the solvent in vacuo. Treat the resulting foam with a mixture of $CH_3OH:EtOAc:CH_2Cl_2$ and filter the resulting precipitate. Suspend this precipitate in $CH_2Cl_2$ (80 ml), wash 3 times with 2.5M aqueous NaOH, then with water, and dry over anhydrous $Na_2SO_4$. Yield: 0.54 g of the title compound. Purify the filtrate by flash chromatography ($SiO_2$) using 2½% $CH_3OH(NH_3)$/EtOAc as eluent to yield another 0.58 g of product. Total yield: 1.12 g (58%).

HRMS (FAB): Calculated for $C_{13}H_{19}N_2O_2S$ $(M+H)^+$: 267.1167; found: 267.1174.

Preparation 3

1'-[5-[[3,5-Dichlorophenyl]methoxy]-3-(3,4-dichlorophenyl)-4-oxopentyl]-1,2-dihydro-spiro[3H-indole-3,4'-piperidine]

Add a solution of HBr (gas) in acetic acid (3.0 ml) to phenylmethyl 1'-[3-(3,4-dichlorophenyl)-5-[(3,5-dichlorophenyl)methoxy]-4-oxopentyl]-1,2-dihydro-spiro [3H-indole-3,4'-piperidine]-1-carboxylate [0.250 g, 0.34 mmoles) dissolved in glacial acetic acid (2.0 ml). Stir the solution at room temperature for 4 h, then add $Et_2O$ (30 ml). Decant the liquid and wash the resultant solid with $Et_2O$. Suspend the solid in water (10 ml) and add 1.0M aqueous KOH (5.0 ml). Extract the mixture with $Et_2O$ (3×30 ml), combine the extracts, wash with water and dry ($Na_2SO_4$). Remove the solvent and purify the reaction mixture by preparative thin layer chromatography ($SiO_2$), eluting the plates twice with ETOAc:hexanes:$CH_3OH(NH_3)$ (15:85:3). Extract the desired product with 5% $CH_3OH(NH_3)$/EtOAc. Yield: 57 mg.

Mass Spectrum (FAB): 591($^{35}Cl+^{37}Cl$ isotope), 593 (M+H) ($^{35}Cl+^{37}Cl$ isotope), 595 ($^{35}Cl+^{37}Cl$ isotope).

EXAMPLE 1

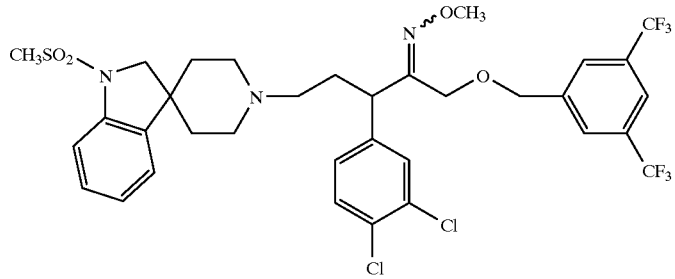

1'-[5-[[3,5-Bis(trifluoromethyl)phenyl]methoxy]-3-(3,4-dichlorophenyl)-4-(methoxyimino)pentyl]-1,2-dihydro-1-(methylsulfonyl)-spiro[3H-indole-3,4'-piperidine]

Use the method described in Procedure A to prepare the title compound. HRMS (FAB) $(M+H)^+$: calc'd for $C_{34}H_{35}N_3O_4SCl_2F_6$: 765.1630; found: 765.1610.

EXAMPLE 2

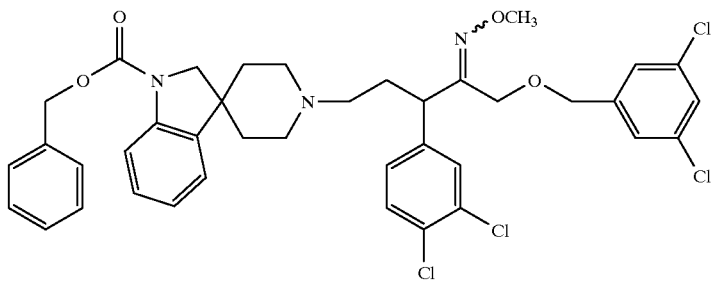

41

Phenylmethyl 1'-[3-(3,4-dichlorophenyl)-5-[[3,5-dichlorophenyl]methoxy]-4-(methoxyimino)pentyl]-1,2-dihydro-spiro[3H-indole-3,4'-piperidine]-1-carboxylate

Use the method described in Procedure A to prepare the title compound. HRMS (FAB) (M+H)$^+$: calc'd for $C_{39}H_{40}N_3O_4Cl_4$: 754.1773; found: 754.1757.

EXAMPLE 3

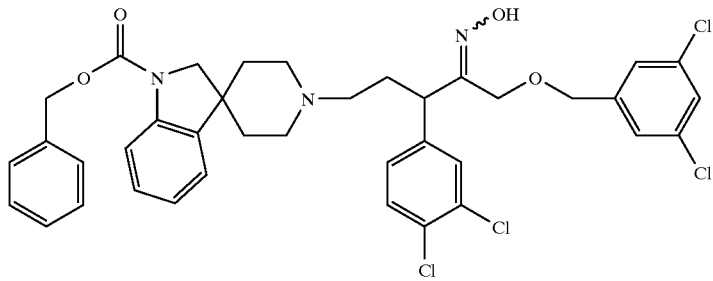

Phenylmethyl 1'-[3-(3,4-dichlorophenyl)-5-[[3,5-dichlorophenyl]methoxy]-4-(hydroxyimino)pentyl]-1,2-dihydro-spiro[3H-indole-3,4'-piperidine]-1-carboxylate

Use the method described in Procedure A to prepare the title compound. HRMS (FAB) (M+H)$^+$: calc'd for $C_{38}H_{38}N_3O_4Cl_4$: 740.1616; found: 740.1625.

EXAMPLE 4

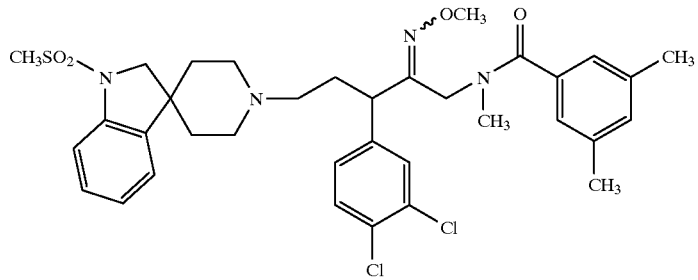

Step 1:

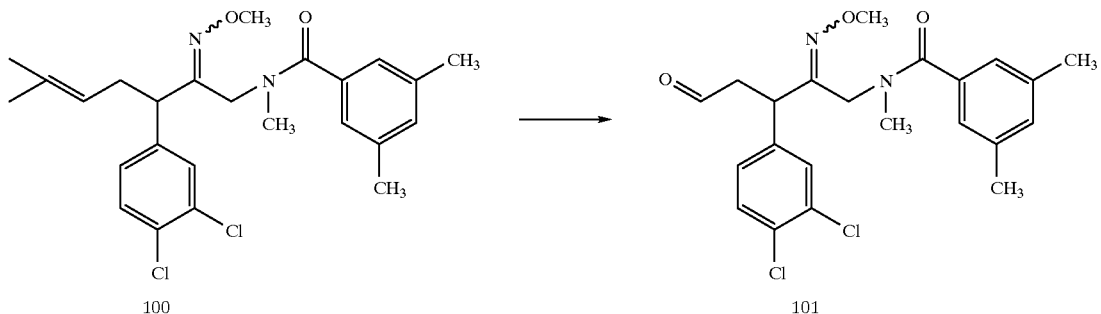

42

Cool a solution of 100 (10.21 g, 0.5 mmol) in EtOAc (3.6 ml) to −78° C. and subject the solution to a subsurface flow of $O_2$, then $O_3$ (0.4, 1 min.), then $O_2$ for 0.5 h. Add $(CH_3)_2S$ (1 ml) to quench the reaction, remove the cold bath and allow the mixture to warm to room temperature. Wash the crude mixture with 10% $Na_2S_2O_3$, then brine, dry over $MgSO_4$, filter and concentrate to obtain a light yellow oil (MH$^+$435.0) to be used without further purification in the next step.

Step 2

To a solution of the product of step 1 in $CF_3CH_2OH$ (2.6 ml), add the product of Preparation 2 (1.123 g, 0.46 mmol). When dissolution is complete, add 3Å molecular sieves (0.34 g); after 30 min., add NaCNBH$_3$ (10.17 g, 2.7 mmol). After 2 h, quench the reaction by adding deionized water (10 ml) and stir for 10 min. Partition the reaction mixture between $Et_2O:CH_2Cl_2$ (5:1) and water. Extract the aqueous layer twice with $Et_2O:CH_2Cl_2$ (5:1), wash the combined-

organic layers with brine, dry over MgSO$_4$, filter and concentrate. Purify the crude product by flash chromatography and prep-TLC (twice) to obtain the title compound as a whit foam. Yield: 25.2%. MS: MH$^+$685.3.

EXAMPLE 5

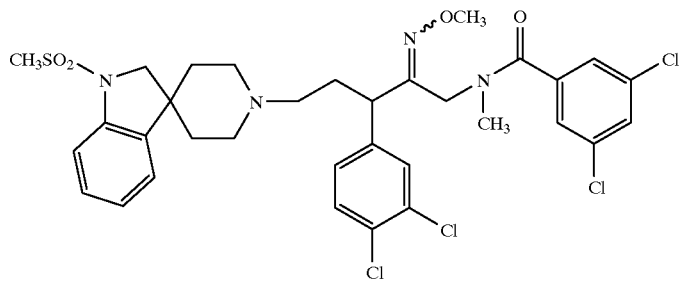

Treat a compound of the formula

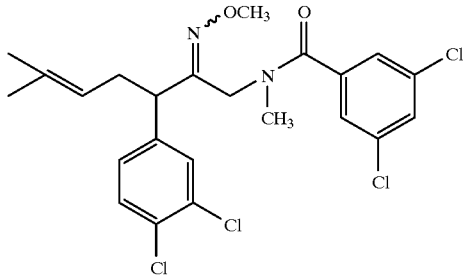

using a procedure similar to that described in Example 4 to obtain the title compound. MS (FAB) 727.2 (100%).

The following formulations exemplify some of the dosage forms of this invention. In each, the term "active compound" refers to a compound of formula I.

Example A

| | Tablets | | |
|---|---|---|---|
| No. | Ingredient | mg/tablet | mg/tablet |
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a course screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

Example B

| | Capsules | | |
|---|---|---|---|
| No. | Ingredient | mg/tablet | mg/tablet |
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

| Sterile Powder for Injection | | |
|---|---|---|
| Ingredient | mg/vial | mg/vial |
| Active sterile powder | 100 | 500 |

For reconstitution add sterile water for injection or bacteriostatic water for injection.

The in vitro and in vivo activity of the compounds of formula I can be determined by the following procedures.

In vitro procedure to identify NK$_1$ activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P potentiates the electrical field stimulated-induced contractions of the guinea pig vas deferens. In unpaired studies, all tissues (control or drug treated) are exposed to cumulative concentrations of Substance P ($1\times10^{-10}$ M–$7\times10^{-7}$ M). Single log-concentrations of the test compounds are given to separate tissues and allowed to equilibrate for 30 minutes before a Substance P concentation-response curve is generated. At least 5 separate tissues are used for each control and individual drug-concentation for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.

Isolated Hamster Trachea $NK_2$ Assay

General methodology and characterization of hamster trachea responses to neurokinin agonists as providing an $NK_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% $O_2$- 5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$- 5% $CO_2$ gas. Tracheal rings are placed under 1.0 g initial tension and allowed a 90 min equilibration period with four 1 $\mu$M NKA challenge, wash and recovery cycles at 20 min intervals. 30 min vehicle pretreatment is followed by cumulative additions of rising doses of NKA (3 nM-1 $\mu$M final concentration, 5 min intervals between additions). The final NKA response is followed by a 15 min wash and recovery period. 30 min pretreatment with a test compound or its vehicle is followed by cumulative additions of rising doses of NKA (3 nM-10 $\mu$M final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 $\mu$M (i.e. $pA_2 \geq 6.0$) are considered actives. Further dose response data is obtained for actives so that an apparent $pA_2$ estimate can be calculated. pA2 is calculated either by estimation of $K_i$ as described by Furchgott (where $pA_2$=–Log $K_i$, R. F. Furchgott, *Pharm. Rev.* 7 [1995] 183) or by Shild Plot Analysis (O. Arunlakshana & H. O. Shild, *Br. J. Pharmacol* 14 [1959] 48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.,* 1, 203–209, 1992) is used to measure airway microvascular leakage (AML). Evans blue (30 mg/kg) is injected intravenously, followed 1 min later by i.v. injection of substance P (10 $\mu$g/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 $\mu$g/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge CA, model MP45-1, range ±2 $cmH_2O$) which measures the pressure-across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, CT, model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 $\mu$g/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 (NK1) of the human neurokinin 2 (NK2) receptors are grown in Dulbecco's minimal essential medium supplemented with 10% fetal calf serum, 0.1 mM non-essential amino acids, 2 mM glutamine, 100units/ml of penicillin and streptomycin, and 0.8 mg of G418/ml at 37° C. in a humidified atmosphere containing 5% $CO_2$.

Cells are detached from T-175 flasks with a sterile solution containing 5mM EDTA in phosphate buffered saline. Cells are harvested by centrifugation and washed in RPMI media at 40° C. for 5 minutes. The pellet is resuspended in Tris-HCl (pH7.4) containing 1 uM phsphoramidon and 4 ug/ml of chymostatin at a cell density of $30\times10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at –80° C.

To assay receptor binding, 50 μl of [³H]-Substance P (9-Sar, 11-Met[02]) (specific activity 41 Ci/mmol) (Dupont-NEN) (0.8 nM for the NK-1 assay) or [³H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 (NK-1) or 1 μM SR-48968 (NK-2) (both synthesized by the chemistry department of Schering-Plough Research Institute). $IC_{50}$ values are determined from competition binding curves and Ki values are determined according to Cheng and Prusoff using the experimentally determined value of 0.8 nM for the NK-1 receptor and 2.4 nM for the NK-2 receptor.

$NK_3$ activity is determined by following a procedure similar to that described in the literature, e.g., *Molecular Pharmacol*, 48 (1995), p. 711–716.

% Inhibition is the difference between the percent of maximum specific binding (MSB) and 100%. The percent of MSB is defined by the following equation, wherein "dpm" is disintegrations per minute:

$$\% \, MSB = \frac{(\text{dpm of unknown}) - (\text{dpm of nonspecific binding})}{(\text{dpm of total binding}) - (\text{dpm of nonspecific binding})} \times 100$$

It will be recognized that compounds of formula I exhibit $NK_1$, $NK_2$ and/or $NK_3$ antagonist activity to varying degrees, e.g., certain compounds have strong $NK_1$ antagonist activity, but weaker $NK_2$ and $NK_3$ antagonist activity, while others are strong $NK_2$ antagonists, but weaker $NK_1$ and $NK_3$ antagonists. While compounds with approximate equipotency are preferred, it is also within the scope of this invention to use compounds of with unequal $NK_1/NK_2/NK_3$ antagonist activity when clinically appropriate.

Using the test procedures described above, compounds of the present invention are found to exhibit a range of activity: percent inhibition at a dosage of 1 μM ranges from about 0 to about 100% inhibition of $NK_1$ and/or about 0 to about 100% inhibition of $NK_2$. Preferred are compounds having a Ki≦100 nM for the $NK_1$ receptor. Also preferred are compounds having a Ki≦100 nM for the $NK_2$ receptor. Another group of preferred compounds are those having a Ki≦100 nM for each of the $NK_1$ and $NK_2$ receptors.

We claim:

1. A compound represented by the structural formula

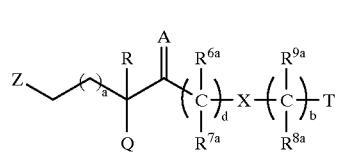

I or a pharmaceutically acceptable salt thereof, wherein:

a is 0, 1, 2 or 3;

b and d are independently 0, 1 or 2;

R is H or $C_{1-6}$ alkyl;

A is =N—OR¹;

X is —C(O)—, —O—, —NR⁶—, —N(R⁶)C(O)—, —C(O)N(R⁶)—, provided that when d is 0, X is —C(O)—, —NR⁶—, —C(O)N(R⁶)— or —N(R⁶)C(O)—;

T is R⁴-aryl;

Q is R⁵-phenyl or R⁵-naphthyl;

R¹ is H, $C_{1-6}$ alkyl, —(C(R⁶)(R⁷))$_n$—G, —(C(R⁶)(R⁷))$_p$—M—(C(R¹³)(R¹⁴))$_n$—(C(R⁸)(R⁹))$_u$—G, or —C(O)N(R⁶)—(C(R¹³)(R¹⁴))$_n$—(C(R⁸)(R⁹))$_u$—G;

R⁴ and R⁵ are independently 1–3 substituents independently selected from the group consisting of H, halogeno, —OR⁶, —OC(O)R⁶, —OC(O)N(R⁶)(R⁷), —N(R⁶)(R⁷), $C_{1-6}$ alkyl, —CF₃, —C₂F₅, —COR⁶, —CO₂R⁶, —CON(R⁶)(R⁷), —S(O)$_e$R¹³, —CN, —OCF₃, —NR⁶CO₂R¹⁶, —NR⁶COR⁷, —NR⁸CON(R⁶)(R⁷), R¹⁵-phenyl, R¹⁵-benzyl, NO₂, —N(R⁶)S(O)₂R¹³ or —S(O)₂N(R⁶)(R⁷); or adjacent R⁴ substituents or adjacent R⁵ substituents can form a —O—CH₂—O— group; and R⁴ can also be R¹⁵-heteroaryl;

R⁶, R⁷, R⁸, R⁶ᵃ, R⁷ᵃ, R⁸ᵃ, R¹³ and R¹⁴ are independently selected from the group consisting of H, $C_{1-6}$ alkyl, $C_2$–$C_6$ hydroxyalkyl, $C_1$–$C_6$ alkoxy-$C_1$–$C_6$ alkyl, R¹⁵-phenyl, and R¹⁵-benzyl; or R⁶ and R⁷, together with the nitrogen to which they are attached, form a ring of 5 to 6 members, wherein 0, 1 or 2 ring members are selected from the group consisting of —O—, —S— and —N(R¹⁹)—;

R⁹ and R⁹ᵃ are independently selected from the group consisting of R⁶ and —OR⁶

R¹⁰ and R¹⁰ᵃ are independently selected from the group consisting of H and $C_{1-6}$ alkyl;

R¹⁵ is 1 to 3 substituents independently selected from the group consisting of H, $C_1$–$C_6$ alkyl, $C_1$–$C_6$ alkoxy, $C_1$–$C_6$ alkylthio, halogeno, —CF₃, —C₂F₅, —COR¹⁰, —CO₂R¹⁰, —C(O)N(R¹⁰)₂, —S(O)$_e$R¹⁰ᵃ, —CN, —N(R¹⁰)COR¹⁰, —N(R¹⁰)CON(R¹⁰)₂ and —NO₂;

$R^{16}$ is $C_{1-6}$ alkyl, $R^{15}$-phenyl or $R^{15}$-benzyl;
$R^{19}$ is H, $C_1$–$C_6$ alkyl, —C(O)N($R^{10}$)$_2$, —CO$_2R^{10}$, —(C($R^8$)($R^9$))$_f$—CO$_2R^{10}$ or —(C($R^8$)($R^9$))$_u$—C(O)N($R^{10}$)$_2$;
f, n and p are independently 1–6;
u is 0–6;
G is selected from the group consisting of $R^4$-heteroaryl, —OR$^6$, —CO$_2R^6$, —CON($R^7$)($R^9$), —C(=NOR$^8$)N($R^6$)($R^7$) and —C(O)N($R^9$)—($R^4$-heteroaryl), provided that when n is 1 and u is 0, or when $R^9$ is —OR$^6$, G is not —OH;
M is selected from the group consisting of —O—, —N($R^6$)—, —C(O)—, —C(O)N($R^9$)— and —N($R^9$)C(O)—, provided that when n is 1, G is not OH; and when p is 2–6, M can also be —N($R^6$)C(=NR$^{25}$)N($R^7$)— or —OC(O)N($R^6$)—;
e is 0, 1 or 2, provided that when e is 1 or 2, $R^{13}$ and $R^{10a}$ are not H;
$R^{25}$ is H, $C_1$–$C_6$ alkyl, —CN, $R^{15}$-phenyl or $R^{15}$-benzyl;
Z is

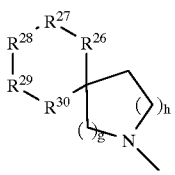

wherein the nitrogen expressly shown above is optionally quaternized with $C_{1-4}$ alkyl or phenyl-$C_{1-4}$ alkyl or is optionally present as the N-oxide

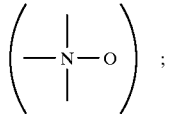

g and h are each independently 0, 1, 2, 3, 4, or 5, with the proviso that g+h is equal to 1, 2, 3, 4, or 5;
$R^{26}$ is selected from the group consisting of
 (1) a covalent bond
 (2) $C_{1-3}$ alkylene, unsubstituted or substituted with a substituent selected from the group consisting of =O, —OH, —OR$^{35}$, halogeno, —CF$_3$, phenyl or mono, di or trisubstituted phenyl, wherein the substituents on the phenyl are independently selected from —OH, —CN, halogeno and —CF$_3$,
 (3) S(O)$_k$
 (4) ($C_{1-3}$ alkylene)—S(O)$_k$
 (5) S(O)$_k$—($C_{1-2}$ alkylene)
 (6) S(O)$_k$NH
 (7) S(O)$_j$—NR$^{35}$
 (8) S(O)$_j$—NR$^{35}$—($C_{1-2}$ alkylene)
 (9) CONH
 (10) CONR$^{35}$—($C_{1-2}$ alkylene)
 (11) CO$_2$ and
 (12) CO$_2$—($C_{1-2}$ alkylene)
wherein j is 1 or 2 and k is 0, 1 or 2;
$R^{27}$ is —NR$^{37}$—, —O—, —S—, —S(O)—, or —SO$_2$—, with the proviso that when $R^{26}$ is a covalent bond and $R^{28}$ is $C_{1-3}$ alkyl, $R^{27}$ must be NR$^{37}$;
$R^{37}$ is selected from a group consisting of:
 (1) H,
 (2) $C_{1-8}$ linear or branched alkyl, unsubstituted, mono-substituted or multiply substituted with —OR$^{35}$,
=O, —NHCOR$^{35}$, —NR$^{35}R^{36}$, —CN, —halogeno, —CF$_3$, -phenyl or substituted phenyl, wherein the substitutents on phenyl are selected from the group consisting of —OH, —CN, halogeno and —CF$_3$;
 (3) S(O)R$^{38}$, wherein $R^{38}$ is $C_{1-6}$ linear or branched alkyl, unsubstituted, mono di or trisubstituted with a substituent selected from the group consisting of =O, —CN, —OR$^{35}$, —NR$^{35}R^{36}$, —NR$^{36}OR^{36}$, -halogeno,—CF$_3$, -phenyl or mono, di or trisubstituted phenyl, wherein the substituents on the phenyl are independently selected from the group consisting of —OH, =O, —CN, —NR$^{35}R^{36}$, —NR$^{35}COR^{36}$, -halogeno, —CF$_3$ and $C_{1-3}$ alkyl;
 (4) SO$_2R^{38}$,
 (5) COR$^{38}$,
 (6) CO$_2R^{38}$,
 (7) CONR$^{36}R^{38}$;
$R^{28}$ is selected from the group consisting of
 (1) a covalent bond
 (2) $C_{1-3}$ alkylene, unsubstituted or substituted with a substituent selected from the group consisting of =O, —OR$^{35}$, halogeno, —CF$_3$, phenyl or mono, di or trisubstituted phenyl, wherein the substitutents on the phenyl are independently selected from the group consisting of —OR$^{35}$, halogeno and —CF$_3$;
 (3) S(O)$_k$
 (4) ($C_{1-3}$ alkylene)—S(O)$_k$
 (5) S(O)$_k$—($C_{1-2}$ alkylene)
 (6) NHS(O)$_j$
 (7) NH($C_{1-2}$ alkylene)—S(O)$_j$
 (8) S(O)$_j$NR$^{35}$
 (9) S(O)$_j$—NR$^{35}$—($C_{1-2}$ alkylene)
 (10) NHCO—($C_{1-2}$ alkylene)
 (11) N R$^{35}$CO
 (12) NR$^{35}$—($C_{1-2}$ alkylene)—CO
 (13) O(CO) and
 (14) ($C_{1-2}$ alkyl)O(CO);
$R^{29}$–$R^{30}$ considered together are 2 adjoining atoms of the ring

said ring being a phenyl, naphthyl or heteroaryl group, and wherein the phenyl, naphthyl or heteroaryl group is unsubstituted, mono, di or tri substituted, wherein heteroaryl is selected from the group consisting of benzimidazolyl, benzofuranyl, benzoxazolyl, furanyl, imidazolyl, indolyl, isoxazolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl and triazolyl; and wherein the substitutents are independently selected from the group consisting of:
 (a) $C_{1-6}$ alkyl, branched or unbranched, unsubstituted or mono or disubstituted by hydroxy
 (b) =O
 (c) OR$^{35}$
 (d) halogeno
 (e) CF$_3$
 (f) NO$_2$
 (g) CN
 (h) NR$^{35}R^{36}$
 (i) NR$^{35}COR^{36}$
 (j) NR$^{35}CO_2R^{36}$
 (k) NR$^{35}S(O)_jR^{36}$
 (l) CONR$^{35}R^{36}$ (m) COR$^{35}$ (n) CO$_2$R$^{35}$ (o) S(O)$_j$R$^{35}$ (p) heteroaryl, or mono or di substituted heteroaryl, wherein heteroaryl is as defined above and the substitutents are selected from the group consisting of: C$_{1-6}$ alkyl, branched or unbranched, unsubstituted or mono or disubstituted by OH; =O; OR$^{35}$; CF$_3$; —NO$_2$; CN; NR$^{35}$R$^{36}$; NR$^{35}$COR$^{36}$; NR$^{35}$CO$_2$R$^{36}$; NR$^{35}$S(O)$_j$R$^{36}$; CONR$^{35}$R$^{36}$; COR$^{35}$; CO$_2$R$^{35}$; S(O)$_j$R$^{35}$; and phenyl; and R$^{35}$ and R$^{36}$ are independently selected from:

(a) H, (b) C$_{1-6}$ alkyl, or mono or disubstituted C$_{1-6}$ alkyl, wherein the substitutents independently selected from the group consisting of phenyl, unsubstituted or substituted with —OH, C$_{1-3}$ alkyl, —CN, halogeno, —CF$_3$ or C$_{1-4}$ alkoxy; —OH; =O; —CN; halogeno; or —CF$_3$;

(c) phenyl, pyridinyl or thiophene, or mono, di or trisubstituted phenyl, pyridinyl or thiophene, wherein the substitutents are independently selected from the group consisting of —OH, C$_{1-4}$ alkyl, —CN, halogeno and —CF$_3$;

(d) C$_{1-3}$ alkyloxy, or

R$^{35}$ and R$^{36}$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, wherein the substituents are independently selected from the group consisting of —OH, =O, —CN, halogeno and —CF$_3$.

2. A compound of claim 1 wherein Q is R$^5$-phenyl, R is H, a is 1,

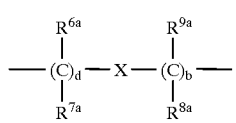

is —CH$_2$—O—CH$_2$, —CH$_2$—N(R$^6$)C(O)—, —CH$_2$NR$^6$CH$_2$— or CH$_2$C(O)NR$^6$—, and Z is

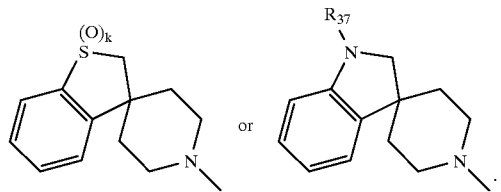

3. A compound of claim 1 wherein X is —O—, —NR$^6$—, —N(R$^6$)C(O)— or —C(O)NR$^6$—; b and d are each 1; and R is H.

4. A compound of claim 3 wherein T is R$^4$-aryl.

5. A compound of claim 3 wherein Q is R$^5$-phenyl.

6. A compound of claim 3 wherein R$^{6a}$, R$^{7a}$, R$^{8a}$ and R$^{9a}$ are each H.

7. A compound of claim 2 wherein T is R$^4$-phenyl and

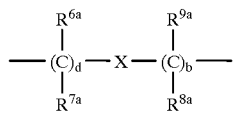

is —CH$_2$—O—CH$_2$ or —CH$_2$—N(R$^6$)C(O)—.

8. A compound of claim 7 wherein R$^1$ is H, alkyl, —(CH$_2$)$_n$—G, —(CH$_2$)$_p$—M—(CH$_2$)$_n$—G or —C(O)N(R$^6$)(R$^7$), wherein M is —O— or —C(O)N(R$^9$)— and G is —CO$_2$R$^6$, —OR$^6$, —C(O)N(R$^6$)(R$^9$), —C(=NOR$^8$)N(R$^6$)(R$^7$), —C(O)N(R$^9$)(R$^4$-heteroaryl) or R$^4$-heteroaryl.

9. The compound represented by the structural formula

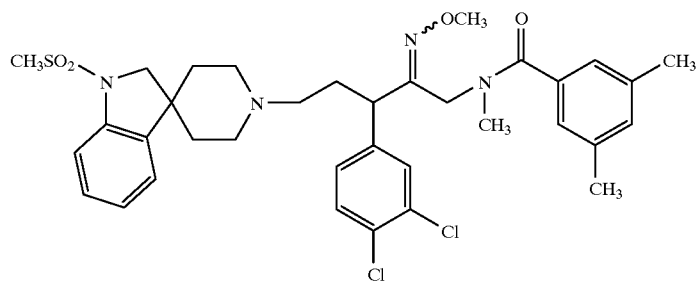

10. A pharmaceutical composition comprising an effective amount of a compound of claim 1 and a pharmaceutically acceptable carrier.

11. A method of treating asthma, cough, bronchospasm, central nervous system diseases, inflammatory diseases and gastrointestinal disorders comprising administering an effective amount of a compound of claim 1 to a mammal in need of such treatment.

12. A compound represented by the formula

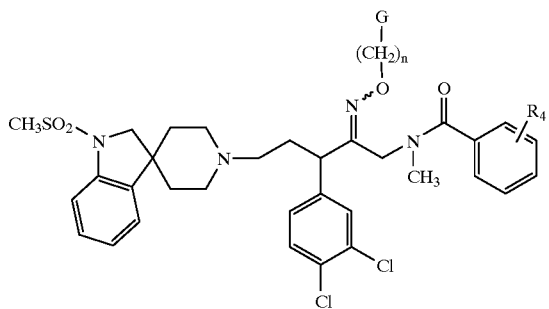

or a pharmaceutically acceptable salt thereof, wherein

G is selected from the group consisting of $R^4$-heteroaryl, $-OR^6$, $-CO_2R^6$, $-CON(R^7)(R^9)$, $-C(=NOR^8)N(R^6)(R^7)$ and $-C(O)N(R^9)-(R^4$-heteroaryl), provided that when n is 1, or when $R^9$ is $-OR^6$, G is not $-OH$;

n is 1–6;

$R^4$ is 1–3 substituents independently selected from the group consisting of H, halogeno, $-OR^6$, $-OC(O)R^6$, $-OC(O)N(R^6)(R^7)$, $-N(R^6)(R^7)$, $C_{1-6}$ alkyl, $-CF_3$, $-C_2F_5$, $-COR^6$, $-CO_2R^6$, $-CON(R^6)(R^7)$, $-S(O)_eR^{13}$, $-CN$, $-OCF_3$, $-NR^6CO_2R^{16}$, $-NR^6COR^7$, $-NR^8CON(R^6)(R^7)$, $R^{15}$-phenyl, $R^{15}$-benzyl, $R^{15}$-heteroaryl, $NO_2$, $-N(R^6)S(O)_2R^{13}$ or $-S(O)_2N(R^6)(R^7)$; or adjacent $R^4$ substituents can form a $-O-CH_2-O-$ group;

$R^6$, $R^7$, $R^8$ and $R^{13}$ are independently selected from the group consisting of H, $C_{1-6}$ alkyl, $C_2-C_6$ hydroxyalkyl, $C_1-C_6$ alkoxy-$C_1-C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of $-O-$, $-S-$ and $-N(R^{19})-$;

$R^9$ is independently selected from the group consisting of $R^6$ and $-OR^6$;

$R^{10}$ and $R^{10a}$ are independently selected from the group consisting of H and $C_{1-6}$ alkyl;

$R^{15}$ is 1 to 3 substituents independently selected from the group consisting of H, $C_1-C_6$ alkyl, $C_1-C_6$ alkoxy, $C_1-C_6$ alkylthio, halogeno, $-CF_3$, $-C_2F_5$, $-COR^{10}$, $-CO_2R^{10}$, $-C(O)N(R^{10})_2$, $-S(O)_eR^{10a}$, $-CN$, $-N(R^{10})COR^{10}$, $-N(R^{10})CON(R^{10})_2$ and $-NO_2$;

$R^{16}$ is $C_{1-6}$ alkyl, $R^{15}$-phenyl or $R^{15}$-benzyl; and $R^{19}$ is H, $C_1-C_6$ alkyl, $-C(O)N(R^{10})_2$, $-CO_2R^{10}$, $-(C(R^8)(R^9))_f-CO_2R^{10}$ or $-(C(R^8)(R^9))_u-C(O)N(R^{10})_2$.

* * * * *